(12) United States Patent
Watanabe et al.

(10) Patent No.: US 6,376,852 B2
(45) Date of Patent: Apr. 23, 2002

(54) SURFACE INSPECTION USING THE RATIO OF INTENSITIES OF S—AND P-POLARIZED LIGHT COMPONENTS OF A LASER BEAM REFLECTED A ROUGH SURFACE

(75) Inventors: Masao Watanabe; Akiko Okubo, both of Tokyo (JP)

(73) Assignee: Advantest Corporation, Tokyo (JP)

( * ) Notice: Subject to any disclaimer, the term of this patent is extended or adjusted under 35 U.S.C. 154(b) by 0 days.

(21) Appl. No.: 09/820,052

(22) Filed: Mar. 28, 2001

Related U.S. Application Data

(62) Division of application No. 09/285,336, filed on Apr. 2, 1999.

(30) Foreign Application Priority Data

| Apr. 3, 1998 | (JP) | 10-091489 |
| Apr. 7, 1998 | (JP) | 10-094504 |
| Jun. 26, 1998 | (JP) | 10-180933 |

(51) Int. Cl.[7] .............................. G01N 21/21; G01J 4/00
(52) U.S. Cl. .................. 250/559.22; 250/225; 356/369; 356/237.2; 356/237.4; 356/237.5
(58) Field of Search ................. 356/237.2, 237.4, 356/237.5, 364, 369; 250/225, 559.22

(56) References Cited

U.S. PATENT DOCUMENTS 4,672,196 A * 6/1987 Canino .................. 356/369
5,835,220 A * 11/1998 Kazama et al. .............. 356/369

* cited by examiner

Primary Examiner—F. L. Evans
Assistant Examiner—Zandra Smith
(74) Attorney, Agent, or Firm—Knobbe Martens Olson & Bear LLP

(57) ABSTRACT

A surface inspection device irradiates a laser beam onto the surface of a sample, scans the surface two-dimensionally, and detects the intensities of the s-polarized light component and p-polarized light component of the reflected laser beam. RR (reflectance ratio), which is the ratio of the reflective intensities of the s- and p-polarized light components, is calculated for each position of the surface of the sample, and the two-dimensional distribution of RR on the surface of the sample is detected. The distribution width of this measured RR is compared with the natural width for a clean sample, and the. surface of the sample is determined to be contaminated when, as the result of comparison, the RR distribution width diverges from the natural width. The absence or presence of contamination on the microscopically rough surface of a sample can therefore be quickly and easily determined based on the RR of the reflective intensities of the s- and p-polarized light components.

15 Claims, 10 Drawing Sheets

US 6,376,852 B2

SURFACE INSPECTION USING THE RATIO OF INTENSITIES OF S— AND P-POLARIZED LIGHT COMPONENTS OF A LASER BEAM REFLECTED A ROUGH SURFACE

This application is a divisional of 09/285,336 filed Apr. 12, 1999.

BACKGROUND OF THE INVENTION

1. Field of the Invention

The present invention relates to a surface inspection device for inspecting the rough surface of a sample, and more particularly to a surface inspection device that inspects the microscopic surface contamination of a sample such as an IC (Integrated Circuit) chip or a processed Silicon wafer or a contact device.

2. Description of the Related Art

In a conventional fabrication process of a semiconductor device, wiring or bonding metal pads have been formed as fine patterns on the surface of a semiconductor chip, and the metal pads are connected to bonding wires or the connection terminals of chip components. Masking materials are applied to the surface of metal pads in the fabrication process, and because this material may hinder electrical connections, cleaning is carried out to remove all traces of the material.

Still, the microscopically rough surface of metal pads complicates the total cleaning of minute contamination from the surface. When the surface of metal pads are contaminated during the fabrication process, this contamination impedes electrical connections and causes insufficient bonding. It is therefore vital in fabricating semiconductor devices to inspect and analyze contamination on the surface of metal pad, investigate the sources of contamination, and then take measures to improve the yield rate of the semiconductor devices.

However, the analysis of minute contamination on the surface of metal pads are made difficult by the microscopically rough surface, as well as their small dimensions. Satisfactory analysis is particularly difficult in cases in which the contaminant is a mixture of organic and inorganic substances.

At present, surface inspection on the nano-scale is presently being carried out using STM (Scanning Tunneling Microscope) or AFM (Atomic Force Microscope) as the basic research in surface inspection of fine structure as described above. Unfortunately, this approach is impractical because it entails considerable time and expense.

Surface inspection is also carried out by a FTIR (Fourier Transform Infrared) spectroscope, which employs the absorption of infrared rays. However, microanalysis by this method is difficult and operation is also complex, and the considerable time and expense thus required for analysis render this method impractical.

One surface inspection method that solves the above-described problems involves analysis by polarized light (ellipsometry), in which surface inspection is realized by irradiating rays onto the surface of a sample to cause reflection and then analyzing the polarized light components of the reflected rays. This method allows microanalysis and simplifies operation.

Ellipsometry allows easy inspection of the surface of a sample but presupposes that the surface of the sample to be inspected is a mirror surface. If the sample is an integrated circuit during fabrication, however, fine metal pads are formed on the mirror surface of a semiconductor wafer by means of sputtering or electroplating, and the surface of the sample becames therefore microscopically rough.

If ellipsometry of the prior art is applied to the surface of this type of sample, accurate inspection is complicated by the diffused reflection of the rays caused by the microscopic bumps and depressions of the surface of the sample. In other words, the surface contamination of the sample, i.e., an integrated circuit during fabrication, cannot be inspected, and the method cannot provide an improvement in the yield rate of integrated circuits.

In addition, defects that occur in the surface of an integrated circuit during fabrication include contamination by inorganic substances, contamination by organic substances, contamination by mixtures of organic and inorganic substances, and the adhesion of extraneous matter. Inspection that can distinguish between these various defects was difficult in the ellipsometry of the prior art.

SUMMARY OF THE INVENTION

It is an object according to the present invention to provide a surface inspection method and device that allow satisfactory inspection and analysis of the surface of a sample such as a semiconductor wafer on which metal pads have been formed without requiring considerable time and expense.

According to one surface inspection method according to the present invention, two-dimensional scanning is effected by irradiating a focused laser beam onto the surface of a sample and then individually detecting the intensities of each of the s-polarized light component and p-polarized light component of the laser beam reflected by each location of the two-dimensionally scanned surface of the sample. The RR (Reflectance Ratio), which is the ratio of the reflected intensities of the detected s-polarized light component and p-polarized light component, is observed for each location of the sample surface, and the distribution of the observed RR on the sample surface is measured. This measured RR distribution width is then compared with the natural width of a clean sample, and the sample surface is determined to be contaminated when, as the comparison results, the RR distribution width diverges from the natural width. In the surface inspection method of this invention, the presence or absence of contamination on the microscopically rough surface of the sample can therefore be accurately and easily determined based on the RR of the reflected intensities of s- and p-polarized light.

The basic principles of the above-described invention are explained hereinbelow. First, in a case in which the sample is the metal pad of a mass-produced circuit component, the sample surface is not microscopically smooth, and the reflection of a laser beam irradiating this surface is generally diffuse. The reflected intensities $R_{os}$ and $R_{op}$ of the s- and p-polarized light can be approximately assumed in this invention as shown below:

$$R_{os} = R_{ou} \times R_s \qquad (1a)$$

$$R_{op} = R_{ou} \times R_p \qquad (1b)$$

where $R_{ou}$ is a specular reflective power on a rough surface, and $R_s$ and $R_p$ are the amplitude reflectances of s- and p-polarized light on an ideally smooth surface observed by means of a Drude reflection equation or a Fresnel reflection equation.

If the sample surface is unevenly contaminated, reflectances $R_s$, and $R_p$ of s- and p-polarized light are subject to complex modification. The ratio of reflective intensities $R_{os}$ and $R_{op}$ by the above-described equations (1a) and (1b) becomes the ratio RR of reflective intensities of s- and p-polarized light as shown in the following equation (2):

$$RR = R_{os}/R_{op} = (R_{ou} \times R_s)/(R_{ou} \times R_p) = R_s/R_p \qquad (2)$$

This ratio RR is independent of the roughness of the sample surface, and the characteristic of the device cancel each other out. However, the s-polarized light and p-polarized light differ from each other in their interaction with the physical surface of the electric vector of light, and the proportion of change in reflective intensity of the s-polarized and p-polarized light due to contaminants is therefore not identical.

In this invention, the state of the sample surface is analyzed using the above-described equation (2) because the use of RR allows the state of contamination to be detected while excluding the effect of the roughness of the sample surface.

The numerical value of the ratio Rs/Rp for the case of a clean sample surface is calculated as a theoretical value from the dielectric constant of the material or the angle of incidence of the beam using a Fresnel reflection equation. If, for example, the angle of incidence is 60°, the theoretical value of RR for gold is 1.09 and 1.95 for rhodium. The state of contamination of the sample surface can be determined by comparison with actually measured values for ratio RR.

The natural width of a clean sample referred to in this invention indicates the distribution width for a case in which RR is determined by detecting the reflective intensities of the s-polarized light component and p-polarized light component for a clean sample surface. This distribution width indicates the width over which the distribution of RR can be compared, and for example, may be the half-width.

According to another surface inspection method of the invention, the distribution of RR on a sample surface is detected as in the above-described surface inspection method of the invention, and the layer thickness of contamination on the sample surface is detected based on the half-width of this measured RR distribution. The surface inspection method of this invention therefore allows accurate and easy determination of the layer thickness of contamination on the microscopically rough surface of the sample based on the RR of the reflective intensities of s- and p-polarized light.

According to yet another surface inspection method of the invention, the distribution of RR on the sample surface is detected as in the above-described surface inspection method of the invention, the central value of this measured RR distribution is compared with a theoretical value observed by means of a Fresnel reflection equation, and the sample surface is determined to be contaminated when, as the result of comparison, the central value of the RR distribution diverges from the theoretical value. The surface inspection method of the invention therefore enables easy and accurate determination of the presence or absence of contamination on the microscopically rough surface of the sample based on the RR of the reflective intensities of the s- and p-polarized light.

According to still another surface inspection method of the invention, the central value of RR distribution is compared with a theoretical value observed by a Fresnel reflection equation as in the above-described surface inspection method of the invention, and the surface of the sample is determined to be contaminated by a single substance when, as the result of comparison, the central value of RR distribution is greater than the theoretical value, and determined to be contaminated by a mixture of substances when the central value of RR distribution is less than the theoretical value. The surface inspection method of the invention therefore determines if the substance that contaminates the microscopically rough surface of the sample is a single substance or a mixture of substances based on the RR of the reflective intensities of the sand p-polarized light.

In one surface inspection device of the invention, a laser beam is focused and irradiated by a laser irradiating device onto the surface of a sample held by a sample holding structure, and at least one of the laser irradiating device and sample holding structure in this state is moved by a relative scanning structure such that the laser beam irradiating the sample scans two-dimensionally. A polarized light detector individually detects the intensities of each of the s-polarized light component and p-polarized light component of the laser beam reflected by each location of the surface of the sample that is scanned two-dimensionally in this way. A ratio observing means observes RR, which is the ratio of the reflective intensities of the s-polarized light component and p-polarized light component for each location of the sample surface, and a distribution detecting means detects the two-dimensional distribution of the observed RR on the surface of the sample. A numerical value comparing means compares the distribution width of RR detected by the distribution detecting means with the natural width of a clean sample, and when, as the result of comparison of this numerical value comparing means, the RR distribution width diverges from the natural width, a contamination judging means determines that the surface of the sample is contaminated. The presence or absence of contamination of the microscopically rough surface of a sample can therefore be determined quickly and easily.

In a surface inspection device according to the foregoing description, the numerical value comparing means may also compare a natural width with the half-width of the RR distribution, which indicates the contamination of the surface of a sample. In this case, the presence or absence of contamination of the surface of the sample can be determined simply and accurately.

In the surface inspection device according to the foregoing description, a layer thickness inspecting means may also detect the layer thickness of contamination on the surface of the sample based on the half-width of the RR distribution detected by the distribution detecting means. In this case, the degree of contamination of the surface of the sample can be determined accurately.

According to another surface inspection device of the invention, a distribution detecting means detects the two-dimensional distribution of RR on the surface of a sample as in the surface inspection device of the invention in the foregoing description, and a numerical value comparing means compares the central value of the RR distribution detected by this distribution detecting means with a theoretical value observed using a Fresnel reflection equation. The contamination judging means determines that the surface of the sample is contaminated when, as the result of comparison of this numerical value comparing means, the central value of RR distribution diverges from a theoretical value. The presence or absence of contamination on the microscopically rough surface of a sample therefore can be determined quickly and easily based on the RR of reflective intensities of the s- and p-polarized light.

In the above-described surface inspection device, it is possible to determine that the surface of the sample is contaminated by a single substance when the central value of the RR distribution is greater than the theoretical value, and contaminated by a mixture of substances when the central value of the RR distribution is lower. In this case, the substance that contaminates the surface of a sample can be determined to be a single substance or a mixture of substances.

In the above-described surface inspection device, it is also possible for an image displaying means to display various data determined based on the RR distribution as an image that corresponds to the surface of a sample. In this case, the two-dimensional contamination of the surface of a sample can be confirmed by means of the displayed image.

According to yet another surface inspection device of the invention, a ratio observing means observes RR for each analyzed region of the surface of a sample as in the above-described surface inspection device of the invention, a frequency detecting means then detects the frequency of occurrence of each value of this observed RR for each prescribed analyzed partition made up of a plurality of analyzed regions, and based on these detection results, a relation detecting means detects the correlation between each value of RR and the frequency of occurrence for each analyzed partition of the sample surface.

This correlation represents the frequency of occurrence of each value of RR in a prescribed analyzed partition of the sample surface and reflects the state of contamination of the sample surface, and the state of contamination of the sample surface therefore can be detected from the above-described correlation. The effect of the microscopic roughness of the surface of a sample can be canceled-because this correlation is detected based on RR, which is the ratio of the reflective intensities of the s-polarized light component and p-polarized light component, and the state of contamination of the surface of a sample can be detected quickly and with good accuracy.

According to still another surface inspection device of the invention, a ratio observing means observes RR for each analyzed region of the surface of a sample as in the above-described surface inspection device of the invention, and a relation detecting means then detects the correlation between each value of the thus-observed RR and a plurality of analyzed regions for each analyzed partition. This correlation represents the frequency of occurrence of each value of RR in a prescribed analyzed partition of the surface of a sample and indicates the state of contamination of the sample surface, and the state of contamination of the surface of a sample can therefore be detected by means of the above-described correlation. The effect of the microscopic roughness of the surface of a sample can be canceled because this correlation is detected based on RR, which is the ratio of the reflective intensities of s-polarized light component and a p-polarized light component, and the state of contamination of the sample surface can therefore be detected quickly and with good accuracy.

In the above-described surface inspection device, a relation detecting means may also generate a two-dimensional graph in which one of the frequency of occurrence and each value of RR is plotted on the vertical axis and the other is plotted on the horizontal axis, and an image displaying means may display the two-dimensional graph generated by this relation detecting means. In this case, the state of contamination of the surface of a sample is displayed as a two-dimensional graph, and the state of contamination of the surface of a sample therefore can be confirmed at a glance by an operator.

In a surface inspection device according to the foregoing description, the relation detecting means may generate a three-dimensional graph in which the analyzed partition is the lower plane and the value of RR for each analyzed region is plotted on the vertical axis, and an image displaying means may display the three-dimensional graph generated by the relation detecting means. In this case, the state of contamination of the surface of the sample is displayed as a three-dimensional graph, and the state of contamination of the sample surface therefore can be confirmed at a glance by an operator.

In a surface inspection device according to the foregoing description, the relation detecting means may generate a two-dimensional graph in which the analyzed partition is represented as a plane and the value of RR for each analyzed region is represented as a prescribed color, and the image displaying means displays the two-dimensional graph generated by the relation detecting means. In this case, the state of contamination of the surface of a sample is displayed as a two-dimensional graph, and the state of contamination of the sample surface therefore can be confirmed at a glance by an operator.

Generally, if the surface of a sample is clean, only specific numerical values of RR are generated at high frequency in concentrations. The sharp decrease in the frequency of occurrence of numerical values diverging from these specific values results in, for example, the steep shape of the curve of a two-dimensional graph.

In contrast, contamination of the surface of a sample brings about changes in the numerical values of RR that are generated at high frequency, and the frequency of occurrence of numerical values that diverge from this numerical value also exhibits a relative increase. As a result, the curve in a two-dimensional graph becomes less steep.

In addition, when the surface of a sample is contaminated as described above, the numerical values of RR that are generated at high frequency also undergo an overall change, and the position of the range in which a numerical values of RR are generated at a prescribed frequency also changes. The numerical values of RR that are generated at high frequency increase when the contamination of the sample surface is inorganic, and the numerical values of RR decrease when the contaminant is organic.

As described in the foregoing explanation, the surface inspection device detects the correlation between the frequency of occurrence and the value of RR for each analyzed partition of a sample surface, or the correlation between the plurality of analyzed regions that make up a prescribed analyzed partition and each value of RR. If these detection results are displayed as a two-dimensional graph or three dimensional graph, the state of contamination of the surface of a sample can be determined from the displayed image.

In a surface inspection method realized by a surface inspection device as described hereinabove, the presence or absence of contamination of the surface of a sample can be determined from the frequency of occurrence of specific numerical values of RR. In this case, the presence or absence of contamination of the sample surface can be determined quickly, easily and with good accuracy.

In addition, the presence or absence of contamination on the surface of a sample can be determined based on the size of the range in which numerical values of RR are generated at a prescribed frequency. In this case, the presence or absence of contamination on the surface of a sample can be determined quickly, easily, and with good accuracy.

In addition, the contamination of a sample can be determined to be caused by an inorganic material when the numerical value of RR at which the frequency of occurrence reaches a peak is higher than a reference numerical value, or caused by an organic material when lower than a reference numerical value. In this case, it can be determined quickly, easily, and with good accuracy whether contamination on the surface of a sample is organic or inorganic.

The contamination of a sample can also be determined as due to an inorganic substance if the position of the range in which a numerical value of RR is generated at a prescribed frequency is higher than a reference position, and due to an organic substance when the position is lower. In this case, it can be determined quickly, easily, and with good accuracy whether contamination on the surface of a sample is organic or inorganic.

Contamination of a sample can also be determined as due to a mixture of organic and inorganic substances if the position of the range in which a numerical value of RR is generated at a prescribed frequency is broader than a reference range. In this case, it can be determined quickly, easily, and with good accuracy that the surface of a sample is contaminated by a mixture of organic and inorganic substances.

As a surface inspection device of the invention that realizes the surface inspection method described hereinabove, the contamination judging means may determine the presence or absence of contamination on the surface of a sample based on the detection results of the relation detecting means. In this case, the surface inspection device can automatically determine the state of contamination of the surface of a sample.

The above-described contamination judging means may also determine if the contamination of a sample is due to an inorganic substance, an organic substance, or a mixture based on the detection results of the relation detecting means. In this case, the surface inspection device can automatically determine the type of contamination of the surface of a sample.

In the above-described surface inspection device, moreover, an intensity comparing means may compare the reflective intensity of the s-polarized light component detected by a polarized light detector with a prescribed reference intensity, and when, as the result of comparison, the reflective intensity is lower than the reference intensity, an extraneous material judging means may determine that extraneous material exists in an analyzed partition of the sample surface. In this case, extraneous matter can be detected in a case in which extraneous matter exists in an analyzed partition of the sample surface.

If the presence or absence of extraneous matter is determined for each analyzed partition in this way and if, for example, 400 analyzed regions exist in one analyzed partition, it is preferable that extraneous matter be judged not to exist even though the reflective intensity of the s-polarized light component is lower than the reference intensity in several analyzed regions, and that extraneous matter be judged to exist when the reflective intensity of the s-polarized light component is lower than the reference intensity in several hundred analyzed regions.

In a surface inspection device as described hereinabove, an operation controlling means may nullify the detection results for an analyzed partition in which the extraneous matter judging means has determined the existence of extraneous matter. This nullification of detection results presents the unnecessary work of analyzing contamination in analyzed partitions in which extraneous matter adheres to the surface of a sample, and therefore enables an improvement in both absolute work efficiency and the accuracy of analysis of contamination.

According to another surface inspection method of the invention, a laser beam is focused and irradiated onto the surface of a sample, and the intensity is detected of at least one of the s-polarized light component and p-polarized light component of the laser beam reflected by the surface of the sample. The reflective intensity on a rough surface can be calculated by dividing this detected reflective intensity by the reflective intensity of a corresponding polarized light component on a smooth surface, and the roughness of the surface of the sample is calculated from the reflective intensity calculated by this intensity calculating means. In this surface inspection method of the invention, therefore, the roughness can be calculated from the reflective intensity of a polarized light component of the surface of the sample.

According to yet another surface inspection method of the invention, a laser beam is focused and irradiated onto the surface of a sample, and the intensities $R_{os}$ and $R_{op}$ of each of the s-polarized light component and p-polarized light component of the laser beam reflected by the surface of the sample are each detected. The reflective intensity at a rough surface $R_{ou}$ is next calculated, this being $\sqrt{[(R_{os} \times R_{op})/(R_s \times R_p)]}$, which is the square root of the ratio of the result $R_{os} \times R_{op}$ obtained by multiplying the detected reflective intensities $R_{os}$ and $R_p$ of the s- and p-polarized light components to the result $R_{os} \times R_p$ obtained by multiplying the reflective intensities $R_s$ and $R_p$ of the s- and p-polarized light components on a smooth surface. The roughness σ of the surface of the sample is then calculated from this calculated reflective intensity $R_{ou}$ and the wavelength λ of the laser beam as $R_{ou} = \exp[-(4\pi\sigma/\lambda)^2]$. In this surface inspection method of the invention, therefore, the roughness can be calculated from the reflective intensities of polarized light components of the sample surface. In particular, surface roughness σ of a sample can be calculated with good accuracy because the reflective intensity of the rough surface $R_{ou}$ is calculated based on both s- and p-polarized light.

The basic principles of the above-described invention are next explained. First, although self-evident from the above-described equations (1a) and (1b), reflective intensity $R_{ou}$ of a rough surface can be calculated even if only one of s- and p-polarized light is measured.

However, greater accuracy is achieved if reflective intensity $R_{ou}$ of a rough surface is calculated based on both s- and p-polarized light as in the following equation (3):

$$R_{ou} = \sqrt{[(R_{os} \times R_{op})/(R_s \times R_p)]} \tag{3}$$

Moreover, the surface of a sample, which is a microscopically rough surface, reflects a laser beam as a generally diffuse beam, as described in the foregoing explanation. The actually measured values of reflective intensities $R_{os}$ and $R_{op}$ of s- and p-polarized light are therefore extremely small numerical values. The actually measured values of reflective intensities $R_{os}$ and $R_{op}$ of s- and p-polarized light are therefore as in the following equations (4a and 4b):

$$R_{os} = P_s/C \tag{4a}$$

$$R_{op} = P_p/C \tag{4b}$$

$P_s$ and $P_p$ are the actual light quantities of incident s- and p-polarized light and C is a device constant, these values being determined based on measurements of a reference sample having a known surface roughness.

Using the above-described equations (4a) and (4b), the previously described equation (3) for reflective intensity $R_{ou}$ of a rough surface becomes:

$$R_{ou} = \{\sqrt{[(R_{os} \times R_{op})/(R_s \times R_p)]}\}/C \tag{5}$$

The parameters of the right side of this equation (5) are all measured values or theoretical values, and reflective intensity $R_{ou}$ of a rough surface is thus calculated. Using statistical theory of surface roughness with this reflective intensity Rou of a rough surface and surface roughness σ results in the following relation:

$$R_{ou}=\exp[-(4\pi\sigma/\alpha\lambda)^2] \qquad (6)$$

The surface roughness σ of a sample is thus calculated.

According to yet another surface inspection method of the invention, the reflective intensity at a rough surface $R_{ou}$ is calculated as $\sqrt{[(R_{os} \times R_{op})/(R_s \times R_p)]}$ as in the above-described surface inspection method of the invention, but roughness σ of the surface of a sample is calculated as $R_{ou}=\exp[-(4\pi\sigma/\alpha\lambda)^2]$ based on this reflective intensity $R_{ou}$, wavelength λ of the laser beam, and corrective coefficient α.

In the surface inspection method of this invention, therefore, roughness can be calculated from the reflective intensities of the polarized light components of the sample surface. In particular, surface roughness σ of a sample can be calculated with good accuracy because reflective intensity $R_{ou}$ of a rough surface is calculated based on both s- and p-polarized light, and the calculation of surface roughness σ of a sample is corrected by corrective coefficient α.

According to still another surface inspection method of the invention, each of the reflective intensities $R_{os}$ and $R_{op}$ of the s-polarized light component and p-polarized light component are individually detected as in the above-described surface inspection method of the invention, and the reflective intensity $R_{ou}$ at a rough surface is calculated as $\{\sqrt{[(R_{os} \times R_{op})/(R_s \times Rp)]}\}/C$, which is the division, by a prescribed device constant C, of the square root of the ratio of the result $R_{os} \times R_{op}$ of multiplying the reflective intensities $R_{os}$ and $P_{op}$ to the result $R_s \times R_p$ of multiplying reflective intensities $R_s$ and $R_p$ of the s-polarized light component and p-polarized light components at a smooth surface. Roughness a of the surface of a sample is calculated from this reflective intensity $R_{ou}$, the laser beam wavelength λ, and corrective coefficient α as $R_{ou}=\exp[-(4\pi\sigma/\alpha\lambda)^2]$.

In the surface inspection method of the invention, roughness of the surface of a sample can be calculated from the reflective intensities of the polarized light components. In particular, the surface roughness σ of a sample can be calculated with good accuracy because reflective intensity $R_{ou}$ of a rough surface is calculated based on both s- and p-polarized light, the calculation of this reflective intensity $R_{ou}$ is corrected by device constant C, and the calculation of surface roughness σ of the sample is corrected by corrective coefficient α.

According to yet another surface inspection device of the invention, when a laser irradiating device focuses and irradiates a laser beam upon the surface of a sample held by a sample holding structure, a polarized light detector detects the intensity of at least one of the s-polarized light component and the p-polarized light component of the laser beam that is reflected by the surface of the sample. An intensity calculating means divides this detected reflective intensity by the reflective intensity of a corresponding polarized light component reflected by a smooth surface to calculate the reflective intensity of a rough surface, and a roughness detecting means calculates roughness of the surface of the sample based on this calculated reflective intensity.

In the surface inspection device of the invention, therefore, roughness can be calculated from the reflective intensity of a polarized light component of the surface of a sample.

According to still another surface inspection device of the invention, when a laser irradiating device focuses and irradiates a laser beam onto the surface of a sample that is held by a sample holding structure, a polarized light detector individually detects the intensities of each of $R_{os}$ and $R_{op}$ of the s-polarized light component and p-polarized light component of a laser beam that is reflected by the surface of the sample. An intensity calculating means calculates reflective intensity $R_{ou}$ of the rough surface as $\sqrt{[(R_{os} \times R_{op})/(R_s \times R_p)]}$, which is the square root of the ratio of the result $R_{os} \times R_{op}$ of multiplying reflective intensities $R_s$ and $R_{op}$ of the detected s- and p-polarized light components to the result $R_s \times R_p$ of multiplying reflective intensities $R_s$ and $R_p$ of the s-polarized light component and p-polarized light component on a smooth surface. Roughness a of the surface of a sample is calculated as $R_{ou}=\exp[-(4\pi\sigma/\lambda)^2]$ based on this calculated reflective intensity $R_{ou}$ and the laser beam wavelength λ.

In this surface inspection device of the invention, therefore, roughness can be calculated from the reflective intensities of the polarized light components of the sample surface. In particular, surface roughness σ of a sample can be calculated with good accuracy because reflective intensity $R_{ou}$ is calculated based on both s- and p-polarized light.

According to yet another surface inspection device of the invention, an intensity-calculating means calculates the reflective intensity $R_{ou}$ of a rough surface as $\sqrt{[(R_{os} \times R_{op})/(R_s \times R_p)]}$ as in the above-described surface inspection device of the invention, and a roughness detecting means calculates roughness σ of the surface of a sample as $R_{ou}=\exp[-(4\pi\sigma/\alpha\lambda)^2]$ based on this calculated reflective intensity $R_{ou}$, the laser beam wavelength λ, and corrective coefficient α.

In the surface inspection device of this invention, roughness can therefore be calculated from the reflective intensities of the polarized light components of the sample surface. In particular, surface roughness σ of a sample can be calculated with good accuracy because reflective intensity $R_{ou}$ of a rough surface is calculated based on both s- and p-polarized light, and because the calculation of surface roughness σ of the sample is corrected by corrective coefficient α.

According to yet another surface inspection device of the invention, an intensity calculating means calculates reflective intensity $R_{ou}$ of a rough surface as $R_{ou}=\{\sqrt{[(R_{os \times Rp})(R_s \times R_p)]}\}/C$ as in the above-described surface inspection device of the invention, and a roughness detecting means then calculates roughness σ of the surface of a sample as $R_{ou}=\exp[-(4\pi\sigma/\alpha\lambda)^2]$ based on this calculated reflective intensity $R_{ou}$, laser beam wavelength λ, and a corrective coefficient α.

In this surface inspection device of the invention, roughness can therefore be calculated from the reflective intensities of the polarized light components of the surface of the sample. In particular, reflective intensity $R_{ou}$ of a rough surface is calculated based on both s- and p-polarized light, and the calculation of this reflective intensity $R_{ou}$ is corrected by device constant C, and the calculation of surface roughness σ of the sample is corrected by corrective coefficient α. Surface roughness o of a sample can therefore be calculated with good accuracy.

In the above-described surface inspection device, a value on the order of 0.2–0.5 is suitable as corrective coefficient α of the roughness detecting means. In this case, surface roughness σ calculated as a theoretical approximate value can be corrected equivalent to the actual numerical value by means of a suitable corrective coefficient α.

In a surface inspection device as described hereinabove, an intensity calculating means may calculate reflective intensities $R_s$ and $R_p$ of s- and p-polarized light components on a smooth surface as $R_s = rs \times rs^*$ and $R_p = rp \times rp^*$ based on Fresnel amplitude reflectances rs and rp and by means of complex conjugate quantity rs* and rp*. In this case, reflective intensities $R_s$ and $R_p$ of s- and p-polarized light components on a smooth surface can be calculated as theoretical values. In addition, Fresnel amplitude reflectances rs and rp are functions that are dependent only on the complex dielectric constant of the metal or semiconductor that is the sample and the incident angle of the laser beam.

In the above-described surface inspection device, a relative scanning structure may move at least one of the laser irradiating device and the sample holding structure to cause the laser beam that irradiates the sample to scan two-dimensionally by prescribed analyzed regions, and an image displaying means may display, as an image that corresponds to the surface of a sample, the multiplicity of roughness values calculated for each of the multiplicity of analyzed regions. In this case, the state of roughness of the surface of a sample can be adequately confirmed by means of the displayed image.

Furthermore, each of the various means described in this invention may be formed so as to realize their functions, and may be formed as, for example, dedicated hardware, a computer provided with appropriate functions by a program, functions realized inside a computer by means of an appropriate program, or a combination of these forms.

The above and other objects, features, and advantages according to the present invention will become apparent from the following description with reference to the accompanying drawings which illustrate examples according to the present invention.

DETAILED DESCRIPTION OF THE PREFERRED EMBODIMENTS

The first embodiment according to the present invention is next explained with reference to FIGS. 1 to 6.

Figure 1:
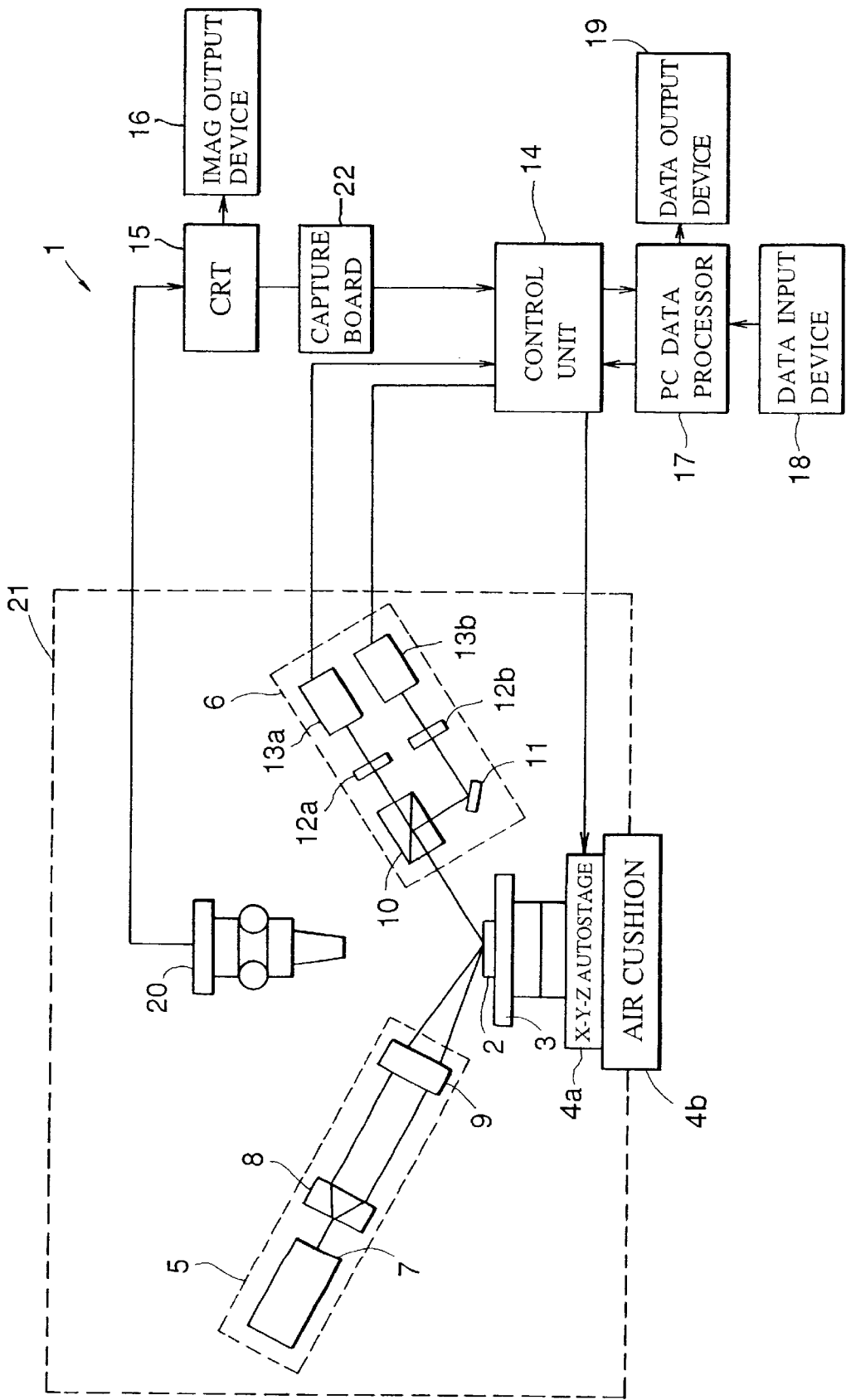
FIG. 1 is a schematic side view of a surface inspection device according to the first embodiment according to the present invention.

Referring to FIG. 1, surface inspection device 1 according to the first embodiment of the invention includes sample holder 3 as a sample holding structure for holding sample 2. Surface inspection device 1 according to this embodiment inspects the surface of sample 2, which is a semiconductor wafer on which fine metal pads are formed of, for example, platinum or copper.

Sample holder 3 is supported so as to allow free movement in the X direction and Y direction and Z direction by X-Y-Z autostage 4a, which is a relative scanning structure, and the X-Y-Z autostage 4a is supported by air cushion 4b.

In addition, both X direction and Y direction are horizontal and orthogonal to each other, the X direction being backward and forward and the Y direction being to the left and right and the Z direction being up and down in this embodiment.

Laser irradiating device 5, which is the laser irradiating device, and polarized light detecting device 6, which is the polarized light detector, are directed at an angle of inclination of about 60° toward one point on the surface of sample 2, which is held in sample holder 3 as described hereinabove, with real image optical microscope 20, which is an image observing device, directed down perpendicularly from directly above.

Laser irradiating device 5 includes: He—Ne (helium-neon) laser tube 7, which is the laser light source; beam expander 8; and focus lens 9. Polarized light detecting device 6 includes: sheet polarizer 10, which is a ray polarizer; plane mirror 11; two pinhole plates 12a, 12b; s-wave photo-detector 13a; and p-wave photo-detector 13b, which is a photoelectric converter.

He—Ne laser tube 7 emits a laser beam of visible light having a wavelength of 633 nm and output of 5.0 mW, and beam expander 8 increases the beam diameter of the laser beam emitted by He—Ne laser tube 7. Focus lens focuses the laser beam increased by beam expander 8. Laser irradiating device 5 thus focuses and irradiates laser beam onto an analyzed region measuring about 5.0 $\mu m^2$ on the surface of sample 2 held by sample holder 3.

Sheet polarizer 10 is made up by a Glan-Thompson prism, each of the s-polarized light component and p-polarized light component from the laser beam reflected by the surface of sample 2 are thus individually extracted.

Pinhole plates 12a, 12b shield the peripheral portions of the s- and p-polarized light components extracted by sheet polarizer 10 such that only the central portions are transmitted, and s- and p-wave photo-detector 13a, 13b detects the reflective intensities of only the central portions of s- and p-polarized light components that are transmitted by pinholes 11.

The X-Y-Z autostage 4a and the laser irradiating device 5 and the polarized light detecting device 6 and the real image optical microscope 20 are covered by cover 21.

One control unit 14 is connected to X-Y-Z autostage 4a, and two photo-detector 13a, 13b, and this control unit 14 integrates and controls the operation of each of the above-described devices. Polarized light detecting device 6 therefore individually detects the intensities of each of the s-polarized light component and p-polarized light component of the laser beam reflected by each location of the two-dimensionally scanned surface of sample 2.

CRT (Cathode-Ray Tube) 15 is connected to real image optical microscope 20, and image output device 16 and capture board 22 are connected to this CRT 15, and the above-described control unit 14 is connected to this capture board 22.

Real image optical microscope 20 observes an analyzed region measuring about 5.0 $\mu m^2$ of the surface of sample 2, CRT 15 generates image data of the surface of sample 2 observed by real image optical microscope 20, and image output device 16 displays the image data of the surface of sample 2 generated by CRT 15.

Control unit 14, which receives the image data from CRT 15, controls the operation of X-Y-Z autostage 4a in accordance with the image data of the analyzed region of the surface of sample 2, whereby the laser beam irradiating sample 2 is caused to scan two-dimensionally.

PC (Personal Computer) data processor 17 is also connected to control unit 14, and data input device 18, such as a keyboard, and data output device 19, such as a display, are connected to this PC data processor 17.

Through manual operation by an operator, data input device 18 applies data input of various data such as command codes to PC data processor 17, and data output device 19 outputs to the operator various data such as display images generated by PC data processor 17.

PC data processor 17 physically includes such components as a CPU (central processing unit), RAM (random access memory), ROM (read only memory), and an I/F (interface); and the CPU reads a control program, which is software stored in an information storage medium such as RAM or ROM and executes various operations to logically realize various functions.

In other words, PC data processor 17 logically realizes the various functions such as the ratio observing function, distribution detecting function, numerical value comparing function, contamination judging function, layer thickness detecting function, and image displaying function.

The ratio observing function is realized through the execution by the CPU of prescribed data processing in accordance with a control program stored in advance in RAM or ROM as described hereinabove; and RR, which is the ratio of the reflective intensities of the s-polarized light component and p-polarized light component detected by polarized light detecting device 6, is thus dected for each analyzed region of the surface of sample 2.

Similarly, through execution by the CPU of prescribed data processing, the distribution detecting function detects the distribution on the surface of sample 2 of RR observed by the ratio observing function. The numerical value comparing function compares the half-width, which is the distribution width of RR detected by the distribution detecting function, with the natural width of a clean sample 2 stored in advance in RAM.

The contamination judging function determines that the surface of sample 2 is contaminated when, as the results of comparison of the numerical value comparing function, the half-width off RR distribution diverges from the natural width; and further, determines that the surface of sample 2 is contaminated by a single substance when the central value of RR distribution is greater than a theoretical value and determines that the surface is contaminated by a mixture of substances when the central value is less.

When it is determined in the above-described contamination judging function that the surface of sample 2 is contaminated by a prescribed substance, layer thickness detecting function detects the layer thickness of contamination on the surface of sample 2 from the half-width of the RR distribution detected by the distribution detecting function.

Image displaying function generates an image corresponding to the surface of sample 2 from the various data of contamination determined based on the RR distribution as described hereinabove and displays this image by means of data output device 19 constituted by a display.

In addition, the various data of contamination that are displayed as an image in this way may take the form of, for example, binary data indicating the presence or absence of contamination, numerical data indicating the layer thickness of contamination, or binary data indicating whether the contaminant is a single substance or a mixture of substances.

The various functions of the above-described PC data processor 17 may be realized by using hardware such as data output device 19 as necessary. Nevertheless, these functions are mainly realized through the operation of a CPU, which is a computer constituted by hardware, in accordance with software stored in an information storage medium such as RAM This type of software is stored in an information storage medium such as RAM as a control program for causing a CPU to execute the operations of: observing RR, which is the ratio of the reflective intensities of the s-polarized light component and p-polarized light component detected by polarized light detecting device 6, for each analyzed region of the surface of sample 2; detecting the distribution of this observed PR on the surface of sample 2; comparing the half-width of this measured RR distribution with a natural width of a clean sample 2; determining that the surface of sample 2 is contaminated when, as the result of comparison, the half-width of the RR distribution diverges from the natural width; determining that the surface of sample 2 is contaminated by a single substance when the central value of RR distribution is greater than a theoretical value and that the surface is contaminated by a mixture of substances when the central value is less than the theoretical value; and finally, generating an image corresponding to the surface of sample 2 based on the various data of contamination determined based on RR distribution and displaying this image by means of data output device 19.

A sequential explanation is next presented regarding the surface inspection method of surface inspection device 1 according to this embodiment in a construction as described hereinabove. First, laser irradiating device 5 focuses and irradiates a laser beam onto the surface of sample 2 held by sample holder 3, and in this state, X-Y-Z autostage 4a moves sample holder 3 such that the laser beam that irradiates sample 2 two-dimensionally scans each analyzed region.

Polarized light detecting device 6 individually detects the intensities of each of s-polarized light component and p-polarized light component of the laser beam reflected by each analyzed region of the surface of sample 2 that is two-dimensionally scanned in this way. PC data processor 17 thus observes the RR, which is the ratio of reflective intensities of the s-polarized light component and p-polarized light component, for each analyzed region of the surface of sample 2.

This PC data processor 17 then detects the distribution of the thus-observed RR on the surface of sample 2, compares the half-width of this measured RR distribution with the natural width of a clean sample 2, and determines that the surface of sample 2 is contaminated when, as the result of this comparison, the half-width of RR distribution diverges from the natural width.

PC data processor 17 further determines that the surface of sample 2 is contaminated by a single substance when the center value of RR distribution is greater than a theoretical value, and determines that the surface is contaminated by a mixture of substances when the center value is less than the theoretical value. The layer thickness of contamination on the surface of sample 2 is detected from the half-width of RR distribution after it has been determined in this way that the surface of sample 2 is contaminated by a prescribed substance.

Figure 6:
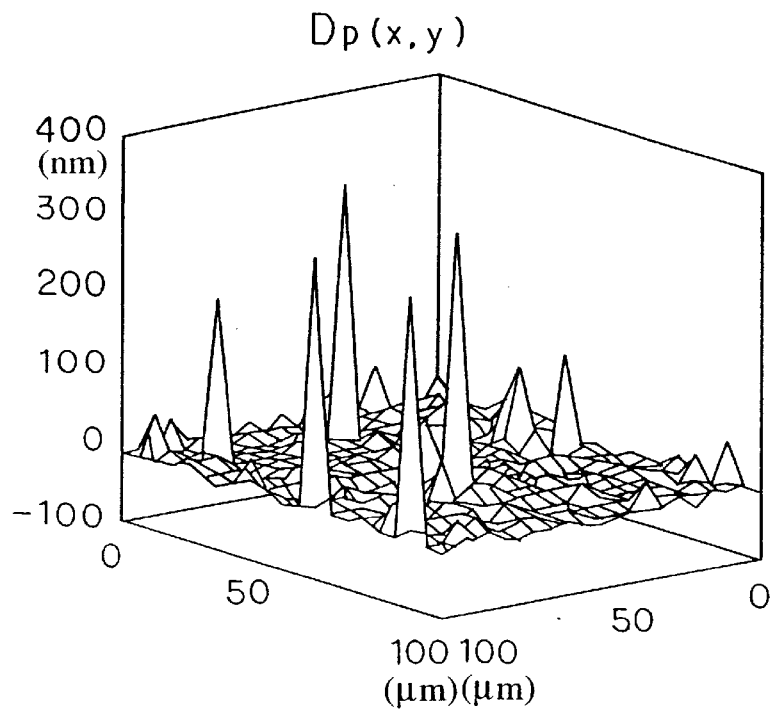
FIG. 6 is a front view showing an image of the film thickness of a contaminant.

PC data processor 17 then generates an image as shown in FIG. 6 corresponding to the surface of sample 2. based on the various data of contamination determined based on RR distribution as described hereinabove, and displays this image by means of data output device 19 constituted by a display.

Figure 2:
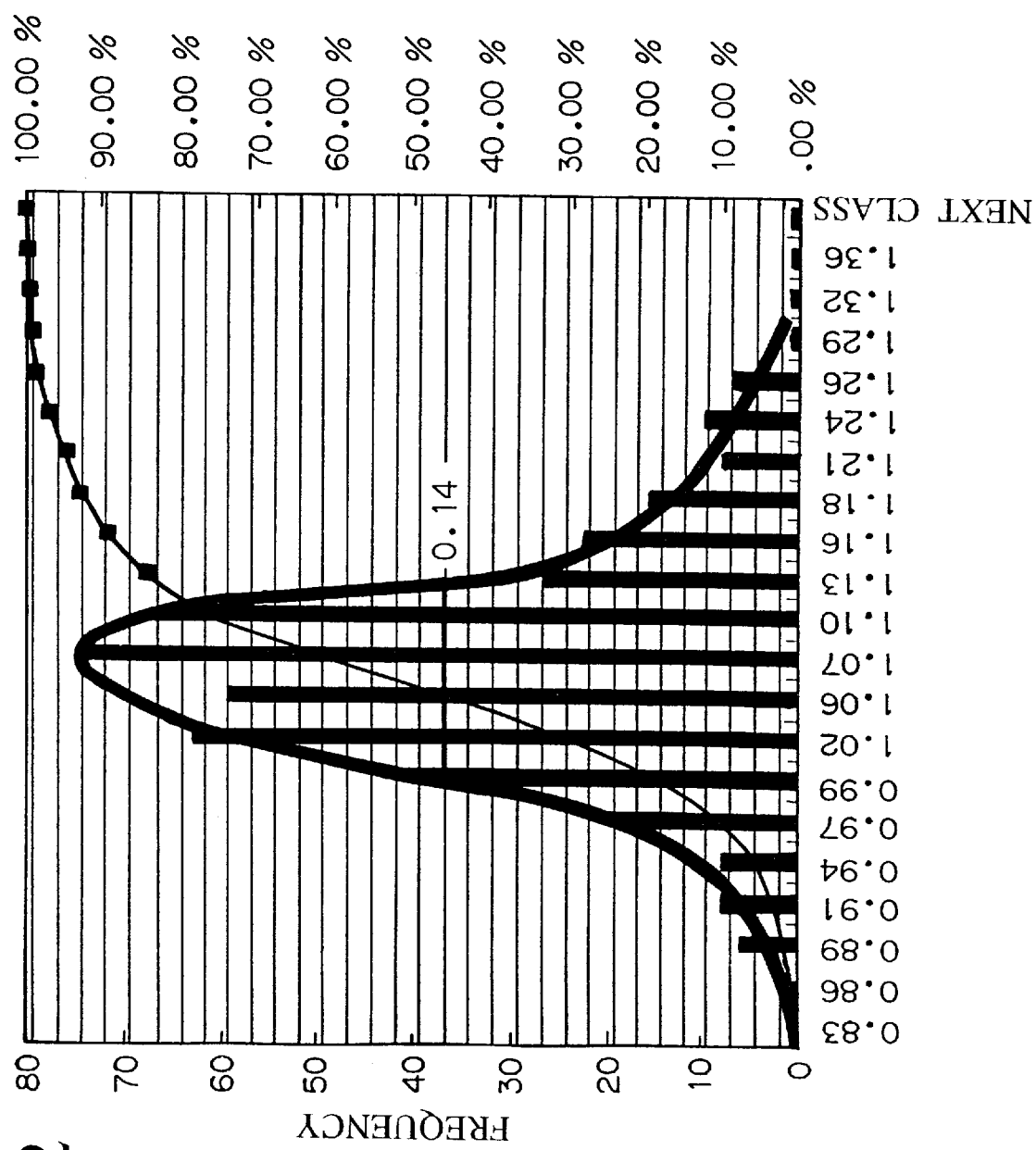
FIG. 2 is a characteristics chart showing RR distribution on the clean surface of a sample.
Figure 3:
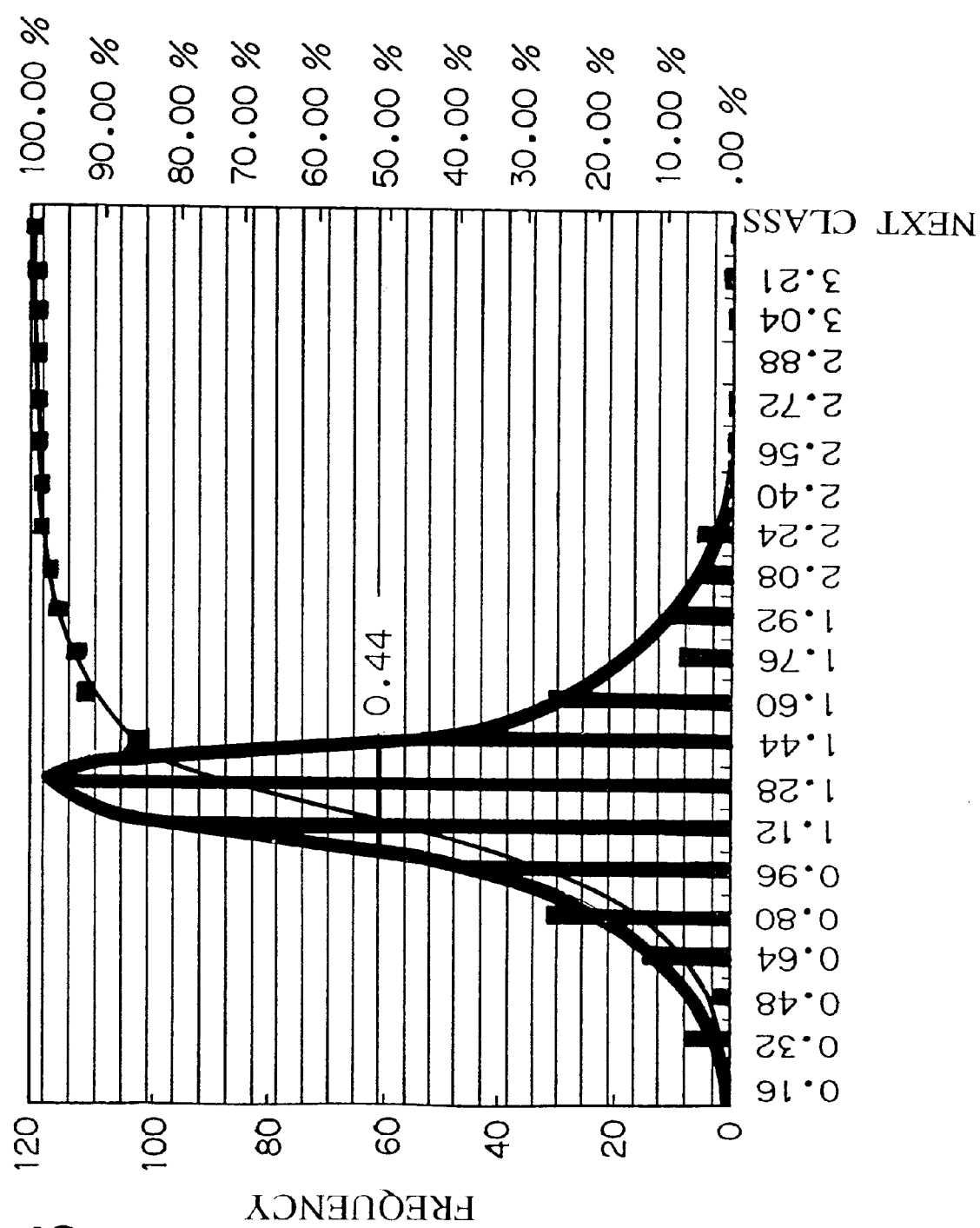
FIG. 3 is a characteristics chart showing RR distribution on the surface of a sample contaminated by a single substance.

For example, if sample 2 has gold metal pad, the natural width, which is the half-width of RR distribution on the clean surface of sample 2, is 0.14, as shown in FIG. 2. If this surface is lightly contaminated by organic molecules of a single substance, the half-width of the measured RR distribution increases to 0.44 as shown in FIG. 3. If the surface is contaminated by a mixture of organic and inorganic substances, the half-width of the measured RR distribution increases to 1.50 as shown in FIG. 4.

Figure 4:
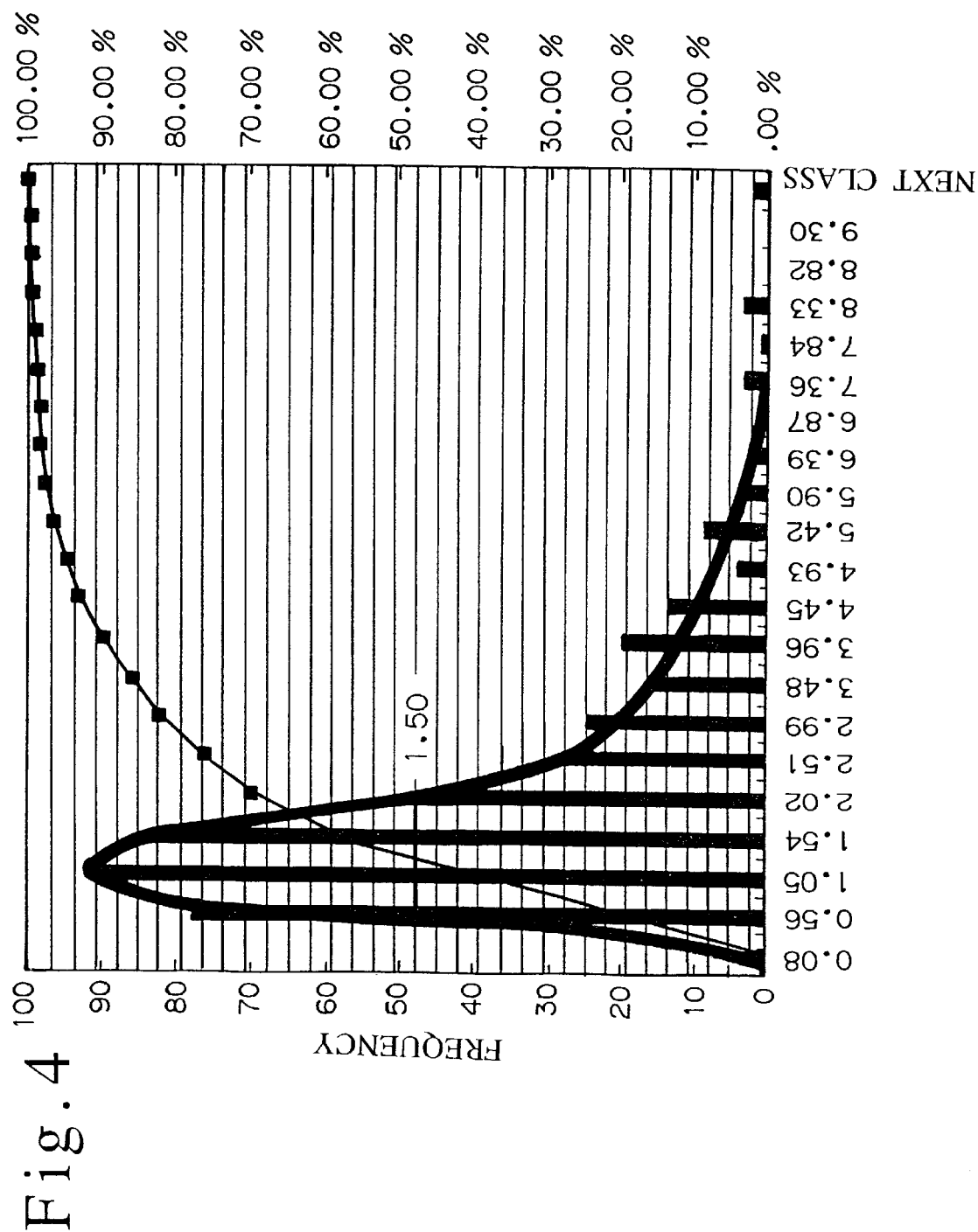
FIG. 4 is a characteristics chart showing RR distribution on the surface of a sample contaminated by a mixture of substances.
Figure 5:
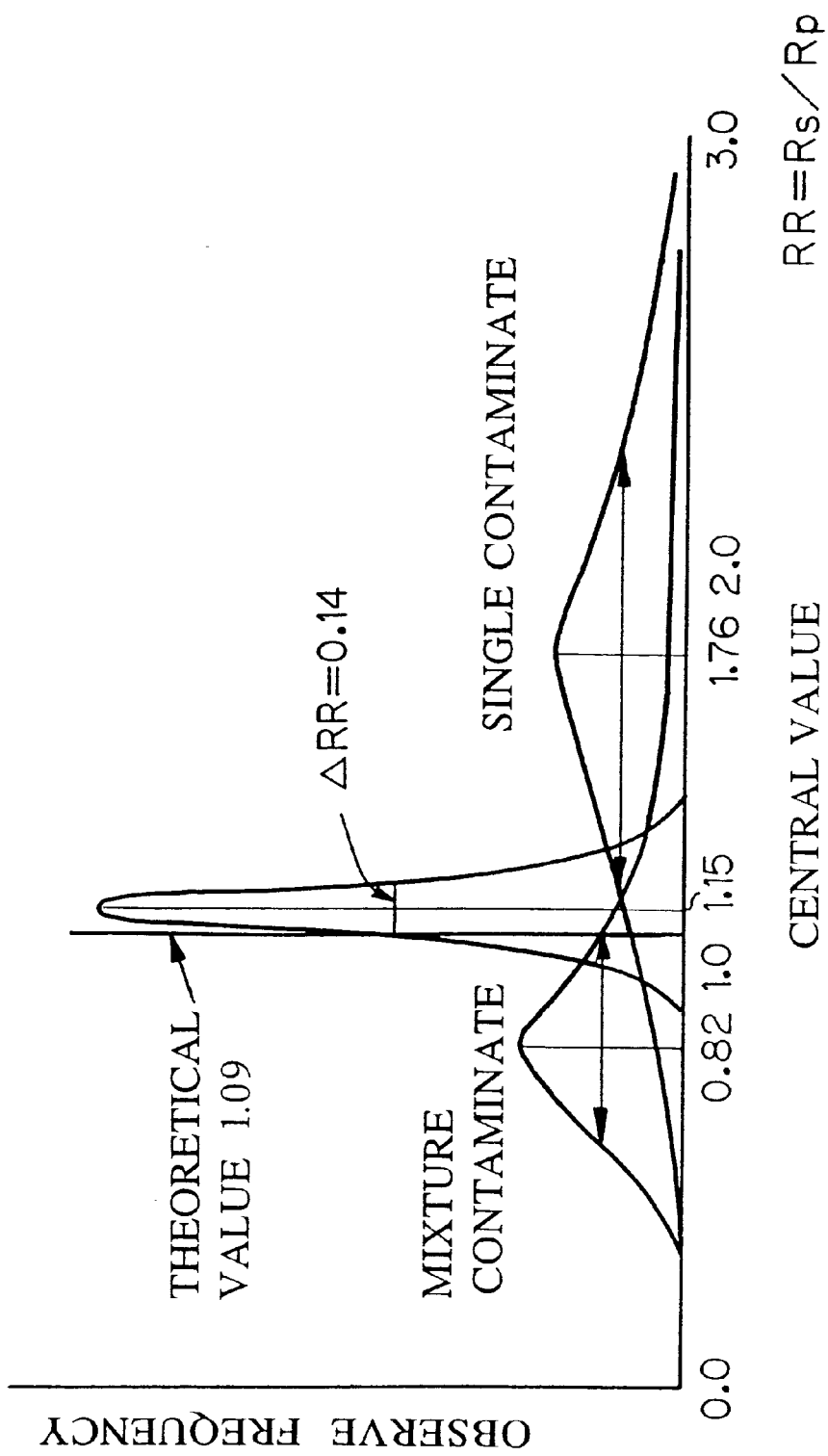
FIG. 5 is a schematic diagram showing the change in RR distribution due to contamination.

In addition, the center value of the RR distribution on a clean surface of sample 2 is 1.07, as shown in FIGS. 2 to 4. This center value increases to 1.28 if the surface is lightly contaminated by a single substance, and decreases to 1.05 if the surface is contaminated by a mixture of substances. In other words, it can be confirmed, as shown in FIG. 5, that when the surface of sample 2 is contaminated by a single substance, the half-width, which is the distribution width of RR, increases and the center value of the distribution range increases. When the surface is contaminated by a mixture of substances, the half-width increases and the center value decreases.

In surface inspection device 1 of this embodiment, the state of contamination of the surface of sample 2, which is microscopically rough, can be analyzed quickly and easily by measuring reflective intensities of s- and p-polarized light components from the surface of sample 2 and detecting the RR distribution as described hereinabove. The invention therefore can contribute to the investigation of sources of contamination during fabrication of a circuit device and thus help to improve the yield of the circuit device.

In the surface inspection device 1 according to this embodiment, moreover, the various data of contamination determined based on RR distribution as described hereinabove are displayed by means of data output device 19 as an image as shown in FIG. 6 that corresponds to the surface of sample 2. An operator can therefore confirm at a glance a three-dimensional representation of the state of contamination of the surface of sample 2. The image of FIG. 6 is a three-dimensional graph showing the layer thickness of contamination made up of remnant mask material when analyzing the surface of gold metal pad as sample 2.

Although an example was described in the above-described embodiment in which X-Y-Z autostage 4a moved the sample holder to bring about scanning of the laser beam that irradiates the surface of sample 2, laser irradiating device 5 or polarized light detecting device 6 may also be moved.

As another example, the laser light source or photo-detector may be fixed and deflecting optics such as a reflecting mirror may be translated or rotated as a method of moving laser irradiating device 5 or polarized light detecting device 6 to cause the laser beam to scan in this way.

In addition, a case was presented in which sheet polarizer 10 is rotated perpendicularly so that each of s- and p-polarized light components are individually detected by polarized light detecting device 6. However, a pair of sheet polarizers having orthogonal directions of polarization may also be arranged alternately on the optical path, or a pair of polarized light detecting devices that individually detect each of the s- and p-polarized light component may also be arranged alternately on the optical path.

In the above-described embodiment, moreover, various functions were logically realized by PC data processor 17 through the operation of a CPU in accordance with a control program that is stored as software in, for example, RAM. However, each of these various functions also may be realized by dedicated hardware, or a portion of these functions may be constituted by software and stored in RAM and a portion constituted by hardware.

The second embodiment of the invention is next explained with reference to the figures. Portions of this second embodiment that are the same as those in the above-described first embodiment are identified by the same name and same reference numerals and redundant detailed explanation of these portions is omitted.

The hardware configuration of surface inspection device 1 according to this second embodiment is identical to that of the first embodiment, but the content of the control program installed in PC data processor 17 is different.

In the surface inspection device 1 of this embodiment, PC data processor 17 logically executes such functions as: a ratio observing function, a frequency detecting function, a relation detecting function, an image displaying function, an intensity comparing function, an extraneous matter judging function, and a operation controlling function.

Through the execution by a CPU of prescribed data processing in accordance with a control program stored in advance in RAM or ROM, the ratio observing function observes RR, which is the ratio of the reflective intensities of the s-polarized light component and p-polarized light component detected by polarized light detecting device 6, for each analyzed region of the surface of sample 2.

The frequency detecting function detects the frequency of occurrence of each value of the observed RR for each prescribed analyzed partition that is made up of a plurality of analyzed regions. For example, if the analyzed region of a laser beam on the surface of sample 2 as described hereinabove is 5.0 $\mu$m$^2$ and an analyzed partition is 100 $\mu$m$^2$, one analyzed partition is made up of 400 analyzed regions.

The relation detecting function detects the correlation between each value of RR and the frequency of occurrence for each analyzed partition of the sample surface based on the detection results of the frequency detecting function, and the image displaying function displays an image of the detection results of the relation detecting function.

In more detail, PC data processor 17 generates a two-dimensional graph as shown in FIGS. 7 to 11 in which each value of RR is plotted on the horizontal axis and the frequency of occurrence is plotted on the vertical axis, and this two-dimensional graph is displayed by means of the display of data output device 19.

The intensity comparing function compares the reflective intensity of the s-polarized light component detected by polarized light detecting device 6 with a prescribed reference intensity that is set in advance, and the extraneous matter function determines that extraneous matter is present in an analyzed partition of the surface of a sample when, as the results of comparison, the reflective intensity is lower than a reference intensity.

When executing work to analyze the state of contamination of the surface of sample 2 by means of the various functions described hereinabove, the operation controlling function first inspects for the presence or absence of extraneous matter by initiating the above-described intensity comparing function and extraneous matter judging function, and then activates the ratio observing function to execute analysis of contamination in an analyzed partition only in cases in which extraneous is determined to be absent.

The operation controlling function halts the work of analyzing the state of contamination of the surface of sample 2 in an analyzed partition in which the existence of extraneous matter has been determined, and, for example, displays both a prescribed guidance message indicating the presence of extraneous matter and position data of the analyzed partition by means of data output device 19.

Software for realizing each of the various functions described hereinabove by PC data processor 17 is stored in an information storage medium such as RAM as a control program for causing the CPU to: compare the reflective intensity of the s-polarized light component detected by polarized light detecting device 6 with a prescribed reference intensity that is set in advance; determine that extraneous matter exists in an analyzed partition of the sample surface when, as the results of this comparison, the reflective intensity is lower than the reference intensity; display a prescribed guidance message by means of the display of data output device 19 when the existence of extraneous matter is confirmed as the result of this determination; when the existence of extraneous matter is negated, observe RR, which is the ratio of the reflective intensities of the s-polarized light component and p-polarized light component detected by polarized light detecting device 6, for each analyzed region of the surface of sample 2; detect the frequency of occurrence of each value of this observed RR for each prescribed analyzed partition, which is made up of a plurality of analyzed regions; generate a two-dimensional graph as the correlation between each value of RR and frequency of occurrence from the results of detection for each analyzed partition of the sample surface; and display this two-dimensional graph on the display of data output device 19.

In a surface inspection method that uses surface inspection device 1 according to this embodiment in the construction described above, a laser beam irradiated onto sample 2 scans each analyzed region two-dimensionally and polarized light detecting device 6 individually detects the intensity of each of the s-polarized light component and p-polarized light component of the reflected laser beam.

However, PC data processor 17 first compares only the reflective intensity of the s-polarized light component with a prescribed reference intensity, and determines that extraneous matter is present in the analyzed partition of the surface of sample 2 if the reflective intensity of this s-polarized light component is lower than the reference intensity.

In this case, PC data processor 17 displays a guidance message indicating the presence of extraneous matter together with position data of the analyzed partition by means of the display of data output device 19, and then halts the work of analyzing contamination in that analyzed partition.

Figure 12:
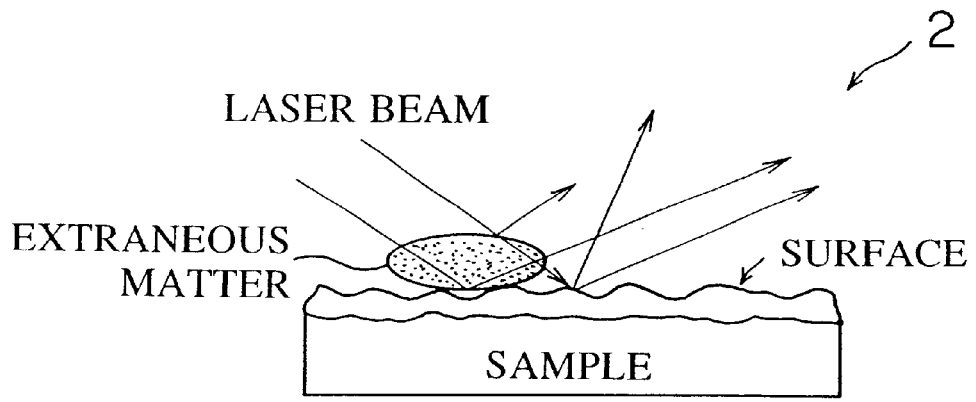
FIG. 12 is a schematic sectional view showing the state of adhesion of extraneous matter to an analyzed partition of a sample surface.

In other words, if extraneous matter is present on the surface of sample 2, the extraneous matter reflects and scatters the irradiating laser beam in different directions than the surface of sample 2 as shown in FIG. 12, and the detected reflective intensity therefore drops sharply. This drop in detected intensity occurs for both s-polarized light component and the p-polarized light component, but the decrease is particularly obvious for the s-polarized light component and the accuracy of detection is therefore improved.

Figure 13:
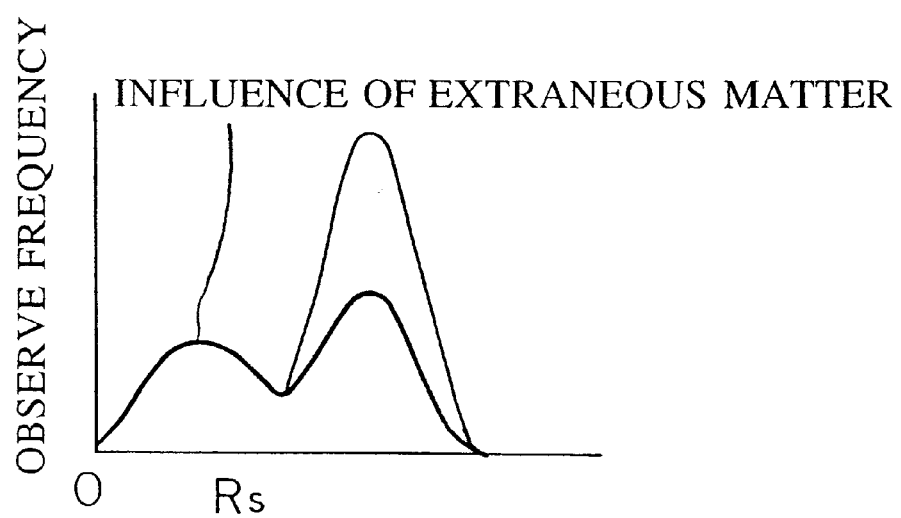
FIG. 13 is a two-dimensional graph showing the correlation between each value of RR and the frequency of occurrence for a surface of a sample to which extraneous matter adheres.

In a case in which operations are executed to analyze contamination in an analyzed partition of the surface of sample 2 in which extraneous matter exists and a two-dimensional graph is generated, the influence of the extraneous matter on the curve of the two-dimensional graph as shown in FIG. 13 prevents a clear indication of the state of contamination. Surface inspection device 1 according to this embodiment therefore does not carry out analysis of contamination in analyzed partitions in which extraneous matter is determined to exist.

On the other hand, if the reflective intensity of the s-polarized light component is higher than the reference intensity, PC data processor 17 determines that extraneous matter is not present in the analyzed partition of the surface of sample 2 and initiates operations for analyzing the contamination of the analyzed partition.

In this case, PC data processor 17 observes RR, which is the ratio of the reflective intensities of the s-polarized light component and p-polarized light component, for each analyzed region of the surface of sample 2, and detects the frequency of occurrence of each value of this observed RR for each analyzed partition.

If the analyzed region of the laser beam on the surface of sample 2 is 5.0 $\mu$m$^2$ and an analyzed partition is 100 $\mu$m$^2$, 400 RR are detected from one analyzed partition and the number of each value of these RR are counted.

When the frequency of occurrence of each value of RR is thus detected for each analyzed partition, a two-dimensional graph is generated in which each value of RR is plotted on the horizontal axis and the frequency of occurrence is plotted on the vertical axis, and this graph is displayed as an image on the display of data output device 19.

The two-dimensional graph displayed as an image in this way represents the frequency of occurrence of each value of RR in the analyzed partition on the surface of sample 2. This image reflects the state of contamination of the analyzed partition on the surface of sample 2, and an operator can judge the state of the surface of sample 2 at a glance by observing the two-dimensional graph.

Figure 7:
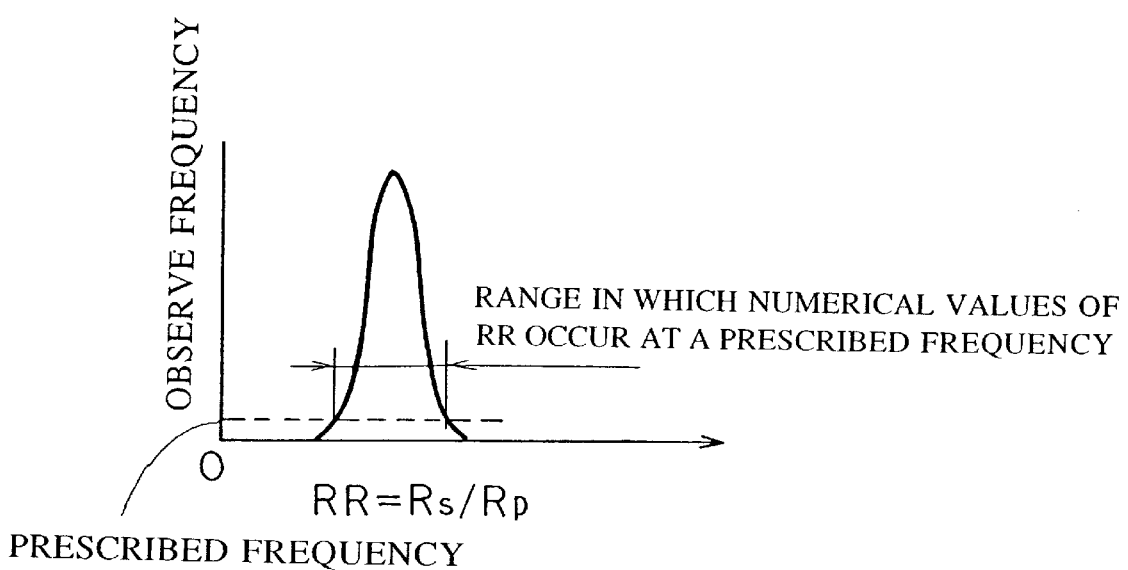
FIG. 7 is a two-dimensional graph displayed by a surface inspection device according to the second embodiment according to the present invention, and is a two-dimensional graph showing the correlation between each value of RR and the frequency of occurrence for the surface of a sample that is clean.

For example, if the analyzed partition of the surface of sample 2 is clean, only specific numerical values of RR occur at high frequency in concentration, and the frequency of occurrence of numerical values that diverge from this value decrease sharply. The curve of the two-dimensional graph therefore takes on a steeply graded narrow concave form as shown in FIG. 7.

Figure 8:
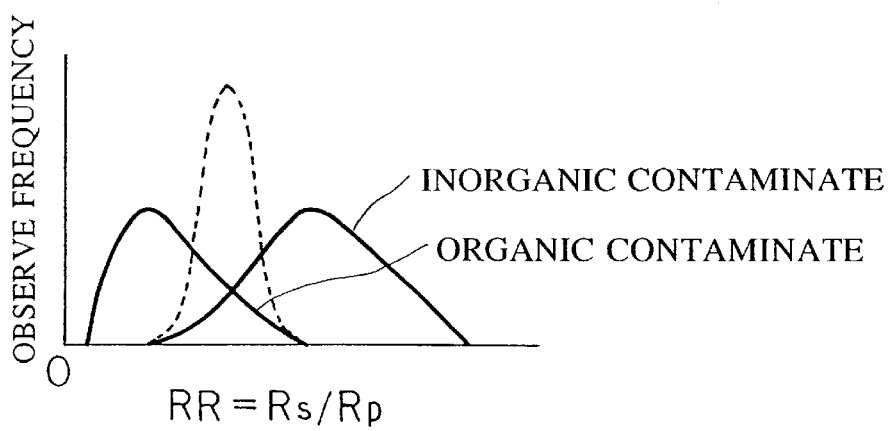
FIG. 8 is a two-dimensional graph showing the correlation between each value of RR and the frequency of occurrence for the surface of a sample that is contaminated by organic and inorganic substances.
Figure 9:
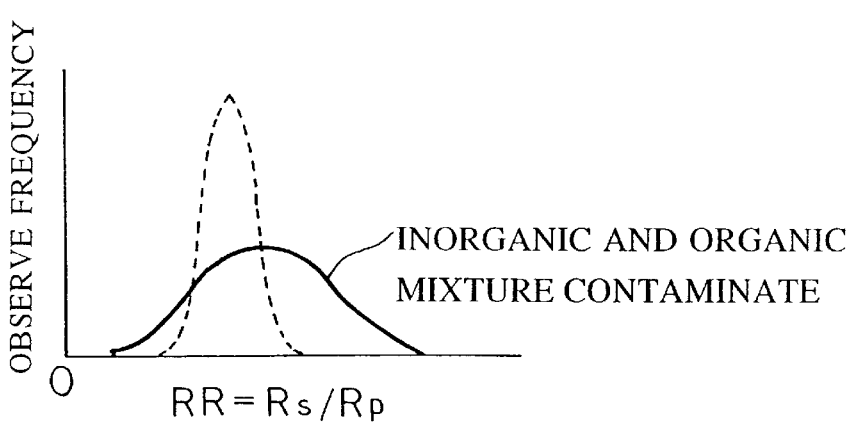
FIG. 9 is a two-dimensional graph showing the correlation between each value of RR and the frequency of occurrence for the surface of a sample that is contaminated by a mixture of substances.

On the other hand, contamination of the surface of sample 2 brings about a decrease in the rate of concentrations of the specific numerical value of RR occurring at high frequency as well as a relative increase in the frequency of occurrence of numerical values that diverge from the specific numerical values, and the form of the curve of the two-dimensional graph therefore becomes broader and less steep as shown in FIG. 8 and FIG. 9.

In addition, the position of the range in which numerical values of RR occur at a prescribed frequency also changes due to the overall change in the numerical values of RR occurring at high frequency when the surface of sample 2 is contaminated as described hereinabove.

In particular, the position of the curve of the two-dimensional graph shifts to the right as shown in FIG. 8 when the contamination of the surface of sample 2 is due to an inorganic substance due to the rise in the numerical values of RR that occurs at high frequency. When the contamination is due to an organic substance, the numerical values of RR decrease and the position of the curve of the two-dimensional graph shifts to the left.

When the contamination of the surface of sample 2 is due to a mixture of organic and inorganic substances, the curve in the two-dimensional graph takes on an extremely broad shape resembling a synthesis of the curves for organic and inorganic substances, as shown in FIG. 9.

Figure 10:
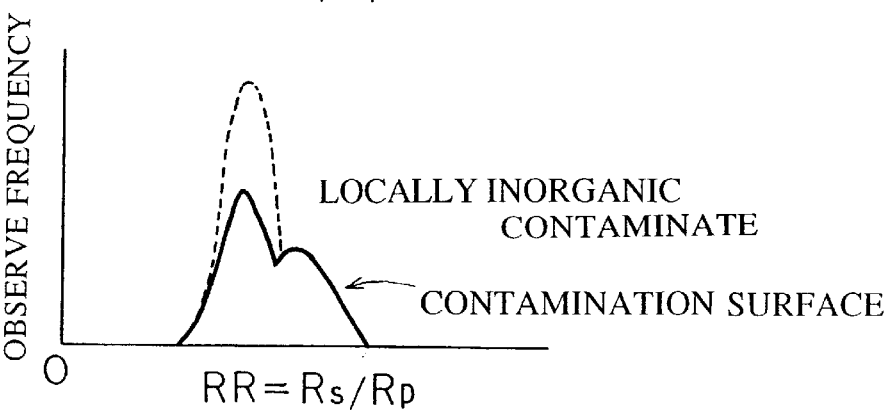
FIG. 10 is a two-dimensional graph showing the correlation between each value of RR and the frequency of occurrence for the surface of a sample that is locally contaminated by an inorganic substance.
Figure 11:
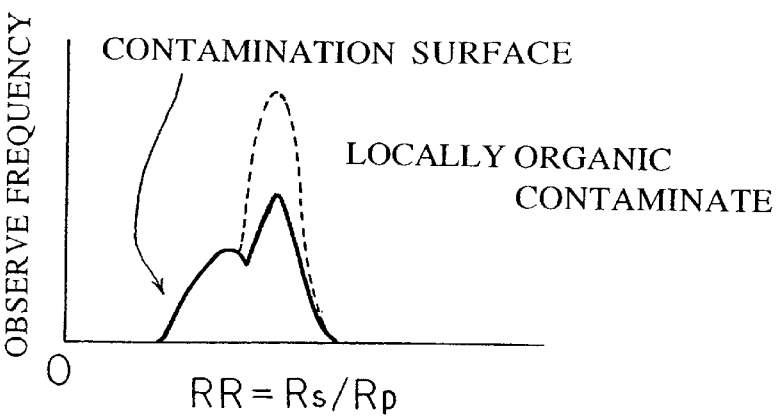
FIG. 11 is a two-dimensional graph showing the correlation between each value of RR and the frequency of occurrence for the surface of a sample that is locally contaminated by an organic substance.

If a portion of the analyzed partition of the surface of sample 2 is locally contaminated, the characteristics of the clean portion and the contaminated portion of the analyzed partition are simultaneously generated in the two-dimensional graph, and the curve in the two-dimensional graph therefore takes on a shape in which a plurality of curves overlap, as shown in FIG. 10 and FIG. 11.

The two-dimensional graph displayed as the results of analysis by surface inspection device 1 as described above enables an operator to confirm at a glance the state of contamination of the surface of sample 2 for each analyzed partition.

In this case, the operator can determine the presence or absence of contamination on the surface of sample 2 based on frequency of occurrence of specific numerical values of RR, and can determine the presence or absence of contamination on the surface of sample 2 based on the size of the range in which numerical values of RR occur at a prescribed frequency.

In addition, the operator can determine that the contamination of sample 2 is due to an inorganic substance if the numerical value of RR at which frequency of occurrence reaches a peak is higher than the reference numerical value, and can determine that the contamination is due to an organic substance if the value is lower. Furthermore, the operator can determine that contamination of sample 2 is due to an inorganic substance if the position of the range at which numerical values of RR occur at a prescribed frequency is higher than a reference position, and can determine that the contamination is due to an organic substance if the position is lower.

Contamination of sample 2 can also be determined as due to a mixture of organic and inorganic substances if the position of the range in which numerical values of RR occur at a prescribed frequency is broader than the reference range, and each of the above-described determinations can be achieved at a glance from the shape of the curve in a two-dimensional graph, the vertical position of the peak, the horizontal position of the peak, the horizontal position of the overall curve, the horizontal width of the entire curve, and the number of peaks.

In the surface inspection method in surface inspection device 1 according to this embodiment, the state of the surface of sample 2 can be detected based on RR, which is the ratio of the reflective intensities of the s-polarized light component and p-polarized light component. The influence of the microscopically rough surface of sample 2 is therefore canceled and good results can be detected.

In this case, the frequency of occurrence of each value of RR is detected for each analyzed partition, and the state of contamination of the surface of sample 2 can be detected effectively. In particular, the results of detection are displayed as a two-dimensional graph that allows the operator to confirm at a glance the state of contamination of the surface of sample 2.

Furthermore, the presence or absence of extraneous matter is detected prior to the work of analyzing the contamination, and analysis of contamination is not carried out for an analyzed partition in which the presence of extraneous matter has been determined. The overall work efficiency is excellent because pointless operations can be omitted, and the state of contamination of the surface of sample 2 can be confirmed with good accuracy because only valid analysis results are outputted.

In particular, the use of the s-polarized light component of the reflected light to realize the above-described detection of extraneous matter eliminates the need for an additional construction dedicated to the detection of extraneous matter and keeps the construction of surface inspection device 1 simple.

Although the display of data output device 19 displays a two-dimensional graph of analysis results in the above-described embodiment, these analysis results may also be printed out by a printer or stored as data to a floppy disk by a floppy disk drive (FDD).

In the above-described embodiment, a case was described in which surface inspection device 1 displays the frequency of occurrence of each value of RR for every analyzed partition as a two-dimensional graph, and in which an operator monitoring this displayed image determines the presence or absence of contamination or the content of contamination of sample 2.

However, fixed rules govern the frequency of occurrence of each value of RR for each analyzed partition as described above according to the existence or content of the contamination, and surface inspection device 1 therefore can determine automatically the presence or absence of contamination, or the content of contamination, by means of a prescribed algorithm.

In the above-described embodiment, moreover, surface inspection device 1 detects the frequency of occurrence of each value of RR for each analyzed partition and generates a two-dimensional graph. However, the correlation between each value of RR and a plurality of analyzed regions may also be detected for each analyzed partition, and a three-dimensional graph or two-dimensional graph may be generated from the detection results.

Figure 14:
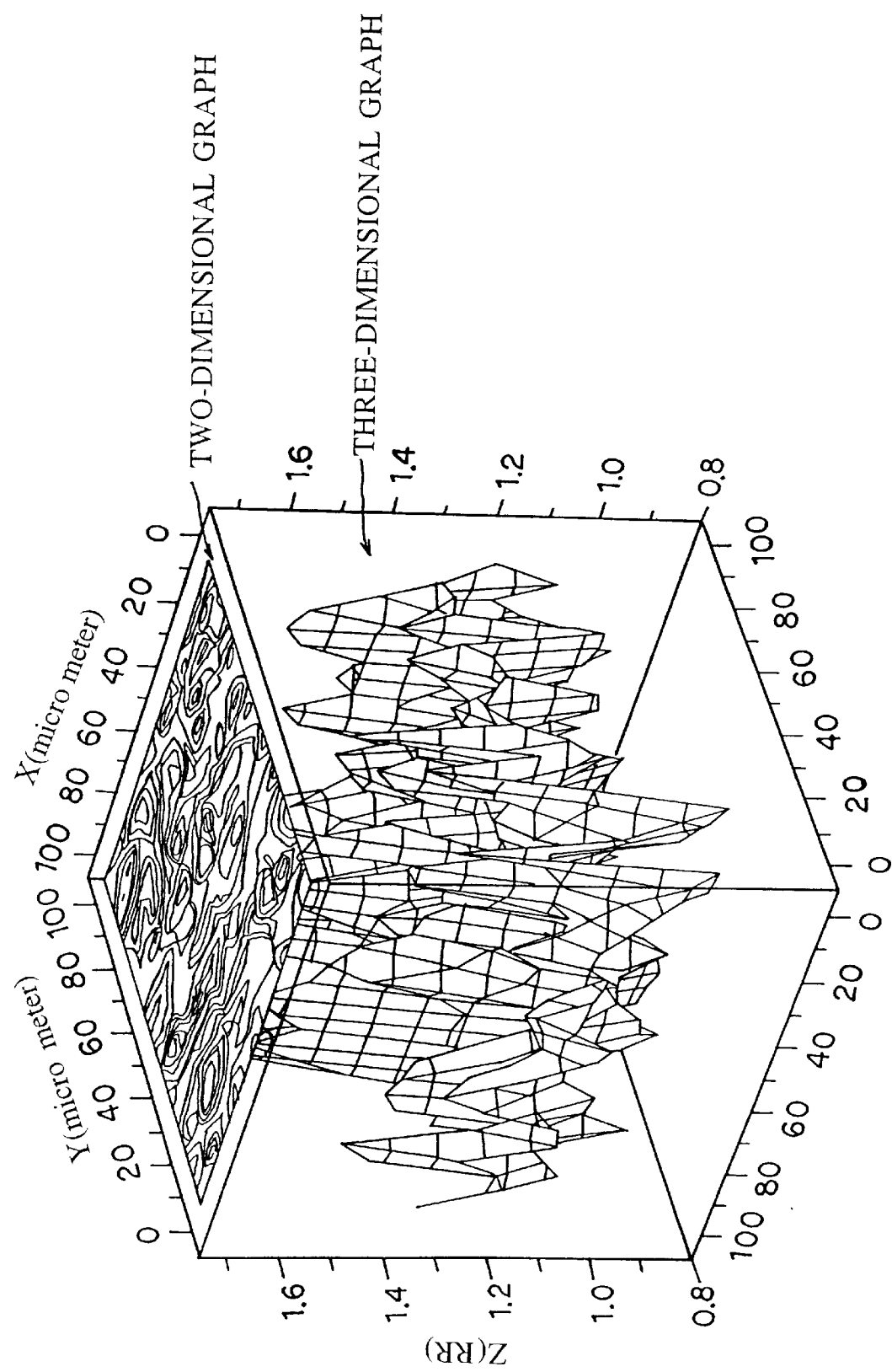
FIG. 14 is a two-dimensional graph and three-dimensional graph showing the correlation between each value of RR and a plurality of analyzed regions that form a prescribed analyzed partition for a surface of a sample that is contaminated.

In this case, a three-dimensional graph may be generated with the analyzed partition as the bottom surface and the value of RR for each analyzed region plotted along the vertical axis as shown in FIG. 14, thereby allowing the state of contamination of the surface of sample 2 to be confirmed at a glance.

Alternatively, the analyzed partition may be represented as a plane with the value of RR for each analyzed region represented by a prescribed color as shown in FIG. 14, and the state of contamination may then be confirmed at a glance from this two-dimensional graph.

The third embodiment of the invention is next explained with reference to the accompanying figures. In this third embodiment as well, parts that are equivalent to those of the above-described first embodiment are identified using the same names and reference numerals and redundant explanation is omitted.

First, the hardware construction of surface inspection device 1 according to this third embodiment is the same as that of the first embodiment, and sample 2 is a connection pad composed of gold in a hybrid IC.

Laser irradiating device 5 focuses a laser beam and irradiates an analyzed region 10–1000 microns square on the surface of sample 2, and the 10–1000 micron-square analyzed region of the surface of sample 2 is observed by real image optical microscope 20.

In the surface inspection device 1 of this embodiment as well, the content of a control program installed in PC data processor 17 is different, and PC data processor 17 logically realizes functions including an intensity calculating function, a roughness detecting function, and an image displaying function.

Through the execution of prescribed data processing by a CPU in accordance with a control program stored in advance in RAM or ROM as described hereinabove, the intensity calculating function calculates the reflective intensity $R_{ou}$ of a rough surface as $R_{ou} = \{\sqrt{[(R_{os} \times R_{op})/(R_s \times R_p)]}\}/C$, which is the division, by a prescribed device constant C, of the square root of the ratio of the result $R_{os} \times R_{op}$ of multiplying reflective intensities $R_{os}$ and $R_{op}$ of the s-polarized light component and p-polarized light component detected by polarized light detecting device 6 to the result $R_s \times R_p$ of multiplying the reflective intensities $R_s$ and $R_p$ of the s- and p-polarized light components reflected by a smooth surface.

Similarly, through the execution of prescribed data processing by a CPU, the roughness detecting function calculates roughness σ of the surface of sample 2 as $R_{ou} = \exp[-(4\pi\sigma/\alpha\lambda)^2]$ from reflective intensity $R_{ou}$ calculated by the above-described intensity calculating function, wavelength λ of the laser beam, and corrective coefficient α.

Figure 15:
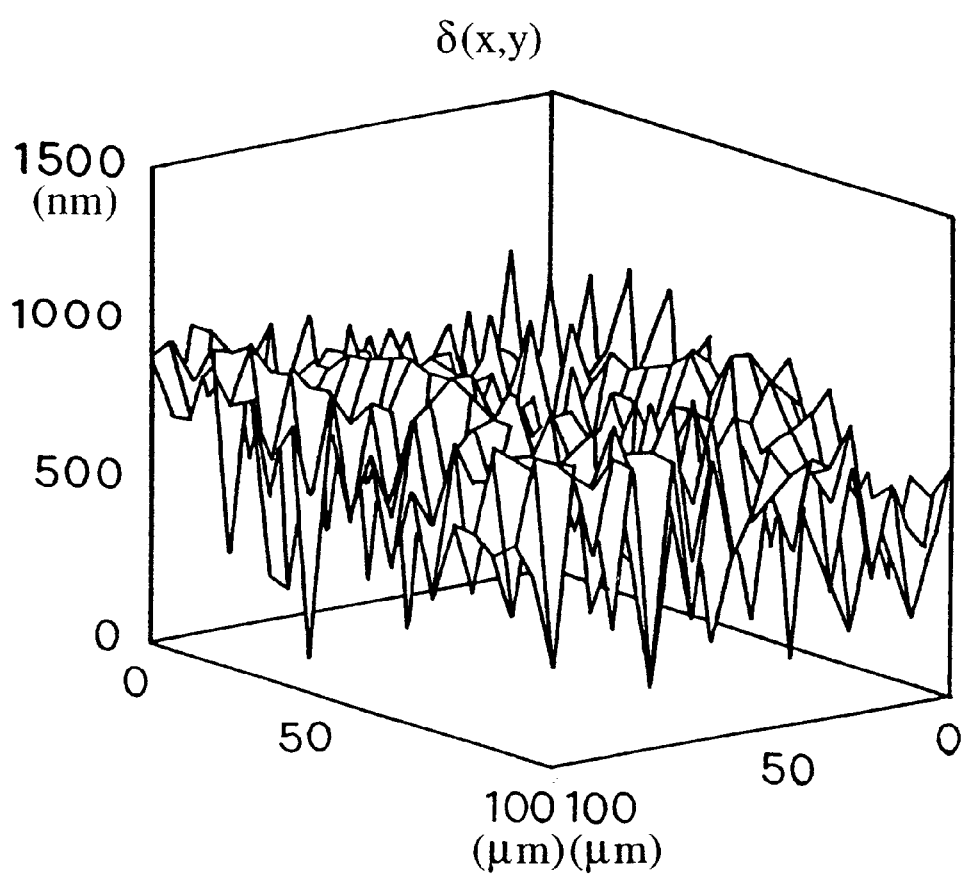
FIG. 15 is a three-dimensional graph of surface roughness of a sample displayed by a surface inspection device according to the third embodiment according to the present invention.

The image displaying function generates a three-dimensional graph that correlates with the surface of sample 2 each of a multiplicity of roughness values calculated for each of a multiplicity of analyzed regions by two-dimensional scanning, and displays this image as shown in FIG. 15 by means of data output device 19, which is constituted by a display.

In the intensity calculating function, device constant C is set in advance based on the results of actual measurement of a reference sample (not shown) having a known surface roughness. In the roughness detecting function, corrective coefficient α is set in advance as 0.2–0.5.

The intensity calculating function calculates the reflective intensities $R_s$ and $R_p$ of the s- and p-polarized light components on a smooth surface as $R_s = rs \times rs^*$ and $R_p = rp \times rp^*$ from Fresnel amplitude reflectances rs and rp and using complex conjugate quantity rs* and rp*.

The software for causing PC data processor 17 to realize each of the above-described functions is stored in an information storage medium such as RAM as a control program for causing a CPU to: calculate reflective intensity $R_{ou}$ on a rough surface as $R_{ou} = \{\sqrt{[(R_{os} \times R_{op})/(R_s \times R_p)]}\}/C$, which is the division, by device constant C, of the square root of the ratio of the result $R_{os} \times R_{op}$ of multiplying reflective intensities $R_{os}$ and $R_{op}$ of the s-polarized light component and p-polarized light component detected by polarized light detecting device 6 to the result $R_s \times R_p$ of multiplying the reflective intensities $R_s$ and $R_p$ of the s- and p-polarized light components on a smooth surface; calculate roughness σ of the surface of sample 2 as $R_{ou} = \exp[-(4\pi\sigma/\alpha\lambda)^2]$ from the thus-calculated reflective intensity $R_{ou}$ wavelength λ of the laser beam, and corrective coefficient α; and correlating to the surface of sample 2 each of the multiplicity of roughness values calculated for each of the multiplicity of analyzed regions by two-dimensional scanning, generating the image of a three-dimensional graph, and displaying the image by data output device 19.

In the surface inspection method that uses surface inspection device 1 according to this embodiment in the above-described construction, a laser beam irradiating sample 2 two-dimensionally scans each analyzed region, and polarized light detecting device 6 individually detects the intensities of each of the s-polarized light components and p-polarized light components of the reflected laser beam.

In PC data processor 17, however, the reflective intensity $R_{ou}$ on a rough surface is calculated as $R_{ou} = \{\sqrt{[(R_{os} \times R_{op})/(R_s \times R_p)]}\}/C$, which is the division, by device constant C, of the square root of the ratio of the result $R_{os} \times R_{op}$ of multiplying reflective intensities $R_{os}$ and $R_{op}$ of the s-polarized light component and p-polarized light component detected by polarized light detecting device 6 to the result $R_s \times R_p$ of multiplying the reflective intensities $R_s$ and $R_p$ of the s- and p-polarized light components on a smooth surface.

Here, the reflective intensities $R_s$ and $R_p$ of the s- and p-polarized light components on a smooth surface are calculated as $R_s = rs \times rs^*$ and $R_p = rp \times rp^*$ from Fresnel amplitude reflectances rs and rp and using complex conjugate quantity rs* and rp*.

Next, roughness σ of the surface of sample 2 is calculated as $R_{ou} = \exp[-(4\pi\sigma/\alpha\lambda)^2]$ from reflective intensity $R_{ou}$ calculated as described hereinabove, wavelength λ of the laser beam, and corrective coefficient α. This roughness σ is calculated for each of the multiplicity of analyzed regions of the surface of sample 2.

A three-dimensional graph image in which the multiplicity of roughness values individually calculated for each of the multiplicity of analyzed regions by two-dimensional scanning are correlated with the surface of sample 2 is generated as shown in FIG. 15, and this image is displayed by data output device 19 constituted by a display.

Surface inspection device 1 according to this embodiment can confirm the roughness of the microscopically rough surface of sample 2 both quickly and easily by measuring the reflective intensities of s- and p-polarized light components on the surface of sample 2 and calculating the surface roughness as described hereinabove. The invention therefore can contribute to the investigation of the sources of contamination during fabrication of a circuit device, and therefore can help in raising the yield of circuit devices.

In particular, in surface inspection device 1 according to this embodiment, reflective intensity $R_{ou}$ of a rough surface is calculated based on both s- and p-polarized light components and the thus-calculated reflective intensity $R_{ou}$ is then corrected by device constant C, and the calculation of surface roughness σ is corrected by an appropriately set corrective coefficient α. Surface roughness σ of sample 2 can therefore be calculated with good accuracy.

Furthermore, in surface inspection device 1 according to this embodiment, the roughness values detected for each of a multiplicity of analyzed regions of the surface of sample 2 as described hereinabove are displayed by data output device 19 as an image that corresponds to the surface of sample 2. An operator can therefore confirm at a glance the state of roughness of the surface of sample 2 from a three-dimensional representation.

The image of FIG. 15 is a three-dimensional graph produced when analyzing the surface of a gold connection pad of a hybrid IC. In actual testing of surface inspection device 1 according to the foregoing description, approximately one minute was required to measure the roughness in 100 analyzed regions of the gold connection pad.

Although a case was described in which the accuracy of calculating surface roughness σ of sample 2 was improved by calculating reflective intensity $R_{ou}$ of a rough surface based on both s- and p-polarized light component in the above-described embodiment, construction of the device can be simplified and the arithmetic processing load reduced by calculating reflective intensity $R_{ou}$ of a rough surface based on only one of the s- and p-polarized light components.

While preferred embodiments according to the present invention have been described using specific terms, such description is for illustrative purposes only, and it is to be understood that changes and variations may be made without departing from the spirit or scope of the following claims.

What is claimed is:

1. A surface inspection method comprising the steps of:
irradiating a focused laser beam onto the surface of a sample;
causing relative movement between the laser beam and the surface of the sample so as to scan a prescribed analyzed partition made up of a plurality of analyzed regions;
individually detecting the intensities of each of the s-polarized light component and p-polarized light component of a laser beam reflected by the surface of a sample that is thus two-dimensionally scanned;
observing RR (Reflectance Ratio), which is the ratio of reflective intensities of the detected s-polarized light component and p-polarized light component, for each analyzed region of the surface of a sample;
detecting, for each analyzed partition, the frequency of occurrence of each value of the observed RR; and
detecting from the detection results correlation between each value of RR and the frequency of occurrence for each analyzed partition of the sample surface.

2. A surface inspection method comprising the steps of:
irradiating a focused laser beam onto the surface of a sample;
causing relative movement between the laser beam and the surface of the sample so as to scan a prescribed analyzed partition made up of a plurality of analyzed regions;
individually detecting the intensities of each of the s-polarized light component and p-polarized light component of a laser beam reflected by the surface of a sample that is thus two-dimensionally scanned;
observing RR (Reflectance Ratio), which is the ratio of reflective intensities of the detected s-polarized light component and p-polarized light component, for each analyzed region of the surface of a sample; and
detecting, for each analyzed partition, a correlation between each of the observed values of RR and analyzed regions.

3. A surface inspection method comprising the steps of:
irradiating a focused laser beam onto the surface of a sample;
causing relative movement between the laser beam and the surface of the sample so as to scan a prescribed analyzed partition made up of a plurality of analyzed regions;
individually detecting the intensities of each of the s-polarized light component and p-polarized light component of a laser beam reflected by the surface of the sample that is two-dimensionally scanned;
determining the existence of extraneous matter in an analyzed partition of the sample surface when the detected reflective intensity of the s-polarized light component is lower than a reference intensity;
observing RR (Reflectance Ratio), which is the ratio of reflective intensities of the s-polarized light component and p-polarized light component, for each analyzed region of the sample surface in analyzed partitions in which the existence of extraneous matter is not determined;
detecting, for each analyzed partition, the frequency of occurrence of each observed value of RR; and
detecting from the results of detection, a correlation between each value of RR and the frequency of occurrence for each analyzed partition of the sample surface.

4. A surface inspection method comprising the steps of:
irradiating a focused laser beam onto the surface of a sample;
causing relative movement between the laser beam and the surface of the sample so as to scan a prescribed analyzed partition made up of a plurality of analyzed regions;
individually detecting the intensities of each of the s-polarized light component and p-polarized light component of a laser beam reflected by the surface of the sample that is two-dimensionally scanned;
determining the existence of extraneous matter in an analyzed partition of the sample surface when the detected reflective intensity of the s-polarized light component is lower than a reference intensity;
observing RR (Reflectance Ratio), which is the ratio of reflective intensities of the s-polarized light component and p-polarized light component, for each analyzed region of the sample surface in analyzed partitions in which the existence of extraneous matter is not determined;
detecting, for each analyzed partition, a correlation between each observed value of RR and the analyzed regions.

5. A surface inspection device comprising:
a sample holding structure for holding a sample;
a laser irradiating device for condensing and irradiating a laser beam onto the surface of a sample held by the sample holding structure;
a relative scanning structure for causing the laser beam that is irradiated onto a prescribed analyzed region of the surface of a sample by the laser irradiating device to scan two-dimensionally;

a polarized light detector for individually detecting the intensities of each of the s-polarized light component and p-polarized light component of a laser beam reflected by each analyzed region of the surface of a sample that is scanned two-dimensionally;

a ratio observing means for observing RR (Reflectance Ratio), which is the ratio of reflective intensities of the s-polarized light component and p-polarized light component detected by the polarized light detector, for each analyzed region of the surface of the sample;

a frequency detecting means for detecting, for each prescribed analyzed partition made up of a plurality of analyzed regions, the frequency of occurrence of each value of RR observed by the ratio observing means; and a relation detecting means for detecting, from the results of detection of the frequency detecting means, a correlation between each value of RR and frequency of occurrence for each analyzed partition of the sample surface.

6. A surface inspection device according to claim 5 that further comprises contamination judging means for determining the presence or absence of contamination of the surface of sample from the results of detection of said relation detecting means.

7. A surface inspection device according to claim 6 wherein said contamination judging means includes means for determining, from the results of detection of said relation detecting means, whether contamination of a sample is due to an inorganic substance, to an organic substance, or to a mixture of organic and inorganic substances.

8. A surface inspection device comprising:
a sample holding structure for holding a sample;
a laser irradiating device for condensing and irradiating a laser beam onto the surface of a sample held by the sample holding structure;
a relative scanning structure for causing the laser beam that is irradiated onto a prescribed analyzed region of the surface of a sample by the laser irradiating device to scan two-dimensionally;
a polarized light detector for individually detecting the intensities of each of the s-polarized light component and p-polarized light component of a laser beam reflected by each analyzed region of the surface of a sample that is scanned two-dimensionally;
a ratio observing means for observing RR (Reflectance Ratio), which is the ratio of reflective intensities of the s-polarized light component and p-polarized light component detected by the polarized light detector, for each analyzed region of the surface of the sample; and
a relation detecting means for detecting a correlation between each value of RR observed by the ratio observing means and the plurality of analyzed regions that form a prescribed analyzed partition.

9. A surface inspection device comprising:
a sample holding structure for holding a sample;
a laser irradiating device for condensing and irradiating a laser beam onto the surface of a sample held by the sample holding structure;
a relative scanning structure for causing the laser beam that is irradiated onto a prescribed analyzed region of the surface of a sample by the laser irradiating device to scan two-dimensionally;

a polarized light detector for individually detecting the intensities of each of the s-polarized light component and p-polarized light component of a laser beam reflected by each analyzed region of the surface of a sample that is scanned two-dimensionally;

a ratio observing means for observing RR (Reflectance Ratio), which is the ratio of reflective intensities of the s-polarized light component and p-polarized light component detected by the polarized light detector, for each analyzed region of the surface of the sample;

a frequency detecting means for detecting, for each prescribed analyzed partition made up of a plurality of analyzed regions, the frequency of occurrence of each value of RR observed by the ratio observing means; and a relation detecting means for detecting, from the results of detection of the frequency detecting means, a correlation between each value of RR and frequency of occurrence for each analyzed partition of the sample surface;
wherein said relation detecting means includes means for generating a two-dimensional graph in which either each value of RR or the frequency of occurrence is the horizontal axis and the other is the vertical axis; and further comprising image displaying means for displaying as an image the detection results of the relation detecting means.

10. A surface inspection device according to claim 9:
wherein said relation detecting means includes means for generating a two-dimensional graph in which an analyzed partition is represented as a plane and the value of RR for each analyzed region is represented as a prescribed color; and further comprising image displaying means for displaying as an image the detection results of the relation detecting means.

11. A surface inspection device comprising:
a sample holding structure for holding a sample;
a laser irradiating device for condensing and irradiating a laser beam onto the surface of a sample held by the sample holding structure;
a relative scanning structure for causing the laser beam that is irradiated onto a prescribed analyzed region of the surface of a sample by the laser irradiating device to scan two-dimensionally;
a polarized light detector for individually detecting the intensities of each of the s-polarized light component and p-polarized light component of a laser beam reflected by each analyzed region of the surface of a sample that is scanned two-dimensionally;
a ratio observing means for observing RR (Reflectance Ratio), which is the ratio of reflective intensities of the s-polarized light component and p-polarized light component detected by the polarized light detector, for each analyzed region of the surface of the sample; and
a relation detecting means for detecting a correlation between each value of RR observed by the ratio observing means and the plurality of analyzed regions that form a prescribed analyzed partition;
wherein said relation detecting means includes means for generating a three-dimensional graph in which an analyzed partition is the bottom surface and RR values for each analyzed region are the vertical axis; and further comprising image displaying means for displaying as an image the detection results of the relation detecting means.

12. A surface inspection device comprising:

a sample holding structure for holding a sample;

a laser irradiating device for condensing and irradiating a laser beam onto the surface of a sample held by the sample holding structure;

a relative scanning structure for causing the laser beam that is irradiated onto a prescribed analyzed region of the surface of a sample by the laser irradiating device to scan two-dimensionally;

a polarized light detector for individually detecting the intensities of each of the s-polarized light component and p-polarized light component of a laser beam reflected by each analyzed region of the surface of a sample that is scanned two-dimensionally;

a ratio observing means for observing RR (Reflectance Ratio), which is the ratio of reflective intensities of the s-polarized light component and p-polarized light component detected by the polarized light detector, for each analyzed region of the surface of the sample;

a frequency detecting means for detecting, for each prescribed analyzed partition made up of a plurality of analyzed regions, the frequency of occurrence of each value of RR observed by the ratio observing means;

a relation detecting means for detecting, from the results of detection of the frequency detecting means, a correlation between each value of RR and frequency of occurrence for each analyzed partition of the sample surface;

intensity comparing means for comparing reflective intensity of an s-polarized light component detected by said polarized light detector with a prescribed reference intensity; and extraneous matter judging means for determining that extraneous matter exists in an analyzed partition of the surface of a sample when, as the comparison results of the intensity comparing means, the reflective intensity is lower than the reference intensity.

13. A surface inspection device according to claim 12 further comprising operation controlling means for nullifying detection results of an analyzed partition in which extraneous matter is determined to exist by said extraneous matter judging means.

14. A surface inspection device comprising:

a sample holding structure for holding a sample;

a laser irradiating device for condensing and irradiating a laser beam onto the surface of a sample held by the sample holding structure;

a relative scanning structure for causing the laser beam that is irradiated onto a prescribed analyzed region of the surface of a sample by the laser irradiating device to scan two-dimensionally;

a polarized light detector for individually detecting the intensities of each of the s-polarized light component and p-polarized light component of a laser beam reflected by each analyzed region of the surface of a sample that is scanned two-dimensionally;

a ratio observing means for observing RR (Reflectance Ratio), which is the ratio of reflective intensities of the s-polarized light component and p-polarized light component detected by the polarized light detector, for each analyzed region of the surface of the sample;

a relation detecting means for detecting a correlation between each value of RR observed by the ratio observing means and the plurality of analyzed regions that form a prescribed analyzed partition;

intensity comparing means for comparing reflective intensity of an s-polarized light component detected by said polarized light detector with a prescribed reference intensity; and extraneous matter judging means for determining that extraneous matter exists in an analyzed partition of the surface of a sample when, as the comparison results of the intensity comparing means, the reflective intensity is lower than the reference intensity.

15. A surface inspection device according to claim 14 further comprising operation controlling means for nullifying detection results of an analyzed partition in which extraneous matter is determined to exist by said extraneous matter judging means.

* * * * *